US007544774B2

(12) United States Patent
Miller et al.

(10) Patent No.: US 7,544,774 B2
(45) Date of Patent: Jun. 9, 2009

(54) MIMOTOPES AND ANTI-MIMOTOPES OF HUMAN PLATELET GLYCOPROTEIN IB/IX

(75) Inventors: Jonathan L. Miller, Syracuse, NY (US); Vicki A. Lyle, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 283 days.

(21) Appl. No.: 11/003,951

(22) Filed: Dec. 3, 2004

(65) Prior Publication Data

US 2005/0153369 A1 Jul. 14, 2005

Related U.S. Application Data

(60) Division of application No. 09/258,947, filed on Mar. 1, 1999, now Pat. No. 7,074,888, which is a continuation-in-part of application No. 08/556,597, filed on Nov. 13, 1995, now Pat. No. 5,877,155, which is a continuation-in-part of application No. 08/406,330, filed on Mar. 17, 1995, now Pat. No. 5,817,748.

(51) Int. Cl.
C07K 5/00 (2006.01)

(52) U.S. Cl. .................. 530/329; 530/328; 530/384; 530/350; 514/2

(58) Field of Classification Search .................. None
See application file for complete search history.

(56) References Cited

U.S. PATENT DOCUMENTS

| 5,114,842 | A | | 5/1992 | Plow et al. |
| 5,122,515 | A | * | 6/1992 | Smith et al. .................. 514/19 |
| 5,177,188 | A | | 1/1993 | Ginsberg et al. |
| 5,817,748 | A | | 10/1998 | Miller et al. |
| 5,877,155 | A | | 3/1999 | Miller et al. |
| 6,126,939 | A | * | 10/2000 | Eisenbach-Schwartz et al. . 424/185.1 |
| 7,074,888 | B1 | | 7/2006 | Miller et al. |

FOREIGN PATENT DOCUMENTS

| WO | WO 91/09614 | | 7/1991 |
| WO | WO 92/09302 | | 6/1992 |
| WO | WO 97/18236 | * | 5/1997 |

OTHER PUBLICATIONS

Stryer, L. Biochemistry, 4th edition, W.H. Freeman and Company, 1995, pp. 18-25.*
Lubben et al., The EMBO Journal, 1992, 11:805-812.*
Balass, M. et al., Proc. Natl. Acad. Sci. USA, 90:10638-10642 (1993).
Califf, R.M. et al., New England Journal of Medicine, 330(14):956-961 (1994).
Christian, R.B. et al., J. Mol. Biol., 227:711-718 (1992).
Collen, D. et al., Thrombosis and Haemostasis, 71(1):95-102 (1994).
Coller, B.S., Annu. Rev. Med., 43:171-180 (1992).
Cwirla, S.E. et al., Proc. Natl. Acad. Sci. USA, 87:6378-6382 (1990).
Ganderton, R.H. et al., Biochem. J., 288:195-205 (1992).
Hobart, M.J. et al., Proc. R. Soc. London. B, 252:157-162 (1993).
Jennings, L.K. et al., Abstract #278, Blood, 84:72a (1994).
Joyce, G.F., Current Opinion in Structural Biology, 4:331-336 (1994).
LaRocca, D. et al., Hybridoma, 11:191-201 (1992).
Lenstra, J.A. et al., J. Immunol. Methods, 152:149-157 (1992).
Mayo, K.H., Trends in Biotechnology, 18:212-217 (2000).
Miller, J.L. et al., Br. J. Haemotol., 74:313-319 (1990).
Miller, J.L. et al., Arteriosclerosis and Thrombosis, 11(5):1231-1236 (1991).
Mousa, S.A. et al., Circulation, 89(1):3-12 (1994).
Otey, C.A. et al., The Journal of Biological Chemistry, 268(28):21193-21197 (1993).
Pearson, W.R., Methods in Enzymology, 183:63-98 (1990).
Pearson, W.R. and Lipman, D.J., Proc. Natl. Acad. Sci. USA, 85:2444-2448 (1988).
Phillips, D.R. et al., Cell, 65:359-362 (1991).
Rote, W.E. et al., Journal of Cardiovascular Pharmacology, 23:681-689 (1994).
Ruan et al., Blood, 69(2):570-577 (1987).
Scott, J.K., Trends in Biochem. Sci., 17:241-245 (1992).
Scott, J.K. and Smith, G.P., Science, 249:386-390 (1990).
Smith, G.P. and Scott, J.K., Methods in Enzymology, 217:228-257 (1993).
South, V. et al., Thrombosis and Haemostasis, 73:144-150 (1995).
Turner, N.A. et al., Abstract #967, Blood, 84:72a (1994).
Ward et al., Leucozyte Typing V: White Cell Differ. Antigens, Proc. Int. Workshop Conf., 5th vol. 2, pp. 1336-1337 Oxford (1995).

* cited by examiner

Primary Examiner—Michael Szperka
(74) Attorney, Agent, or Firm—Peter Rogalskyj, Esq.

(57) ABSTRACT

The present invention is directed to an isolated peptide that functionally mimics a binding site for a monoclonal antibody, the monoclonal antibody recognizing an epitope within the human platelet glycoprotein Ib/IX complex. This peptide is called a mimotope. The invention also provides an isolated molecule capable of binding to the peptide, or the mimotope, which molecule can be an antibody, a second peptide, a carbohydrate, a DNA molecule, an RNA molecule, or other naturally or chemically synthesized molecules. This isolated molecule is called an anti-mimotope. Mimotopes mimicking the binding site for monoclonal antibody C-34 and SZ-2, as well as anti-mimotopes to the C-34 mimotopes, are specifically provided.

11 Claims, 4 Drawing Sheets

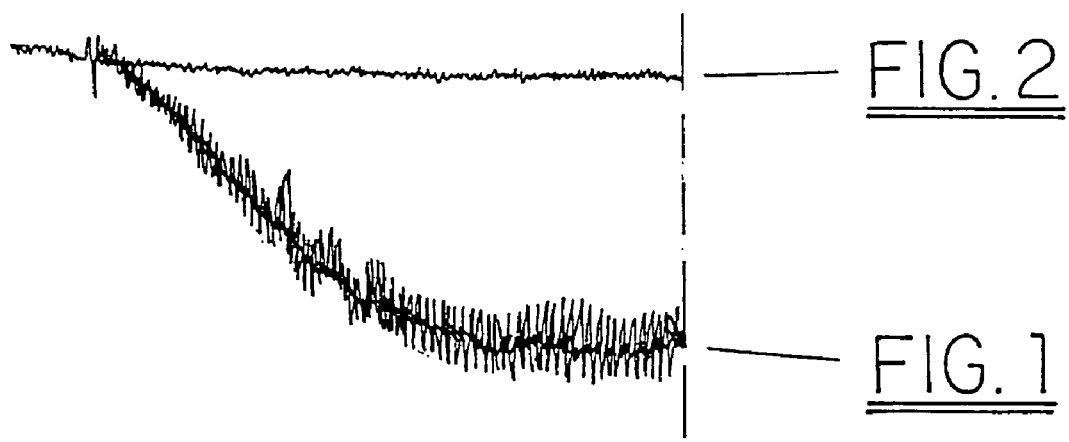
FIG. 2
FIG. 1
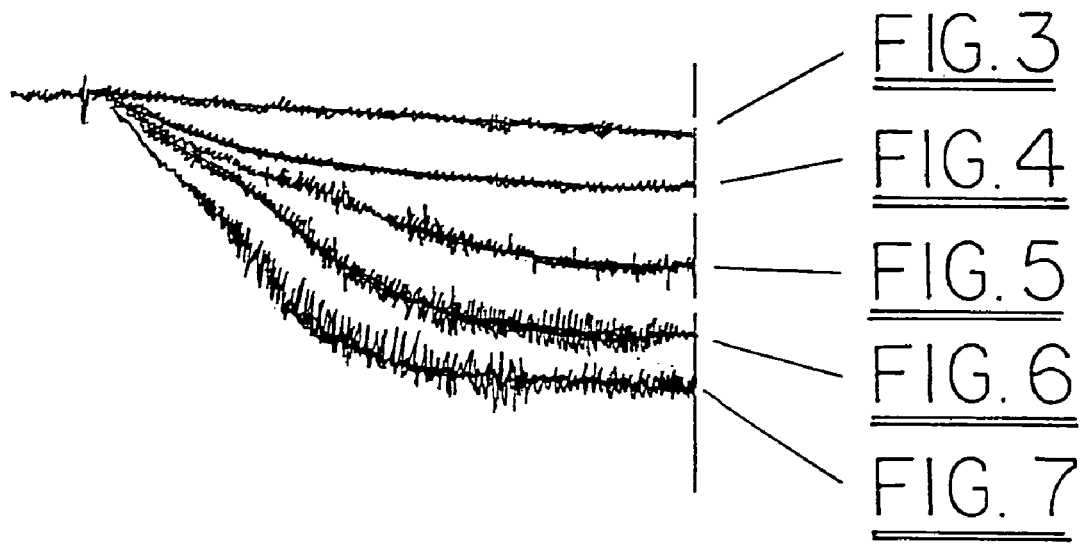
FIG. 3
FIG. 4
FIG. 5
FIG. 6
FIG. 7

FIG. 8

SEQ ID NO: 94:
RHVAWWRQGV though this application various publications are referenced, many in parenthesis. Full citations for these publications are provided at the end of the Detailed Description. The disclosures of these publications in their entireties are hereby incorporated by reference in this application.

SEQUENCE LISTING

```
<160> NUMBER OF SEQ ID NOS: 174

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 1

Ala Trp Asn Trp Arg Tyr Arg Glu Tyr Val
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 2

Lys Trp Asn Trp Arg Asn Lys Lys Tyr Val
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 3

Leu Ser Thr Trp Arg Tyr Phe Glu Tyr Val
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 4

Tyr Leu Gly Trp Arg Tyr Ser Glu Tyr Val
 1               5                  10

<210> SEQ ID NO 5
<211> LENGTH: 10
<212> TYPE: PRT
<213> ORGANISM: Artificial Sequence
```

```
<220> FEATURE:
<223> OTHER INFORMATION: Description of Artificial Sequence:Mimotopes
      and Anti-mimotopes of Human Platelet Glycoprotein Ib/IX

<400> SEQUENCE: 5

Thr Gln Met Trp Arg Ala Arg Glu Tyr Leu
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 6

Trp Arg Gln Arg Glu Tyr Trp Asp Pro Val
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 7

Glu Gly Ser Trp Arg Tyr Arg Lys Gly Gly
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 8

Gly Tyr His Trp Trp Arg Asn Trp Glu Tyr
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 9

Lys Gly Phe Leu Trp Arg Ala Arg Asn Trp
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 10

Met Asn Trp Lys His Trp Arg Ala Arg His
 1               5                  10
```

```
<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 11

Phe Lys Trp Arg Glu Trp Arg Gly Lys Leu
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 12

Pro Asp Arg Gln Val Arg Leu Trp Val Arg
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 13

Arg Val Leu Arg His Trp His Pro Arg Thr
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 14

Gly Arg Arg Val Trp Met Leu Asn His Gly
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 15

Lys Lys Gly Arg His His Val Thr Arg Val
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX
```

```
<400> SEQUENCE: 16

Gly Gly Val Cys Lys Cys Trp Gln Cys Leu
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 17

Phe Ser His Ser Tyr Gly Ser Ala Ile Arg
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 18

Met His Gly His Arg Arg Pro Gly Leu Ala
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 19

Met Ser Lys Lys Pro His Leu Gly Leu Arg
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 20

Thr Met Trp Val Glu Leu Tyr Ser Leu Lys
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 21

Phe Val Asp Pro Gly Arg Ala Gly Arg Gly
 1               5                  10

<210> SEQ ID NO 22
<211> LENGTH: 16
<212> TYPE: PRT
```

<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 22

Cys Cys Leu Leu Pro Leu Gly Phe Tyr Val Leu Gly Leu Phe Trp Leu
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 23

Phe Arg Cys Cys Val Phe Ser Cys Cys Leu Leu Ser
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 24

Gly Phe Arg Cys Leu Val Ser Leu Gly Gly Cys Phe
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 25

Tyr Ser Leu Trp Gly Leu Pro Val Gly Asp Val Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 26

Leu Pro Leu Leu Trp Phe Asn Gly Ala Gly Phe Phe
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 27

Val Trp Gly Leu Phe Arg Gly Leu Glu Asn Gly Ser
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 28

Ser Leu Trp Arg Gln Trp Arg Gly Leu Phe Val Val
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 29

Thr Leu Ser Leu Phe Gly Gly Arg Asp Lys Gly Phe
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 30

Thr Leu Ser Leu Phe Gly Gly Arg Asp Lys Gly Phe
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 31

Met Ser Leu Phe Pro Leu Ser Phe Cys Arg Leu Ile
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 32

Ala Leu Phe Ser Ser Val Trp Gly Asp Val Thr Leu
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

```
<400> SEQUENCE: 33

Gly Trp Phe Gly Pro Phe Trp Val Arg Gly Ser Gly
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 34

Phe Trp Val Ser Val Gly Gly Val Glu Gly Val Val
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 35

Leu Gly Ala Phe Gly Gly Ala Gly Phe Leu Trp Arg
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 36

Cys Arg Gly Ile Val Phe Leu Phe Val Gly Trp Leu
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 37

Phe Trp Leu Val Lys Gly Ala Gly Ala Trp Arg Phe
 1               5                  10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 38

Trp Asn Trp Arg Tyr Arg Glu Tyr Val
 1               5

<210> SEQ ID NO 39
<211> LENGTH: 12
```

```
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 39

Gln Val Arg Leu Trp Ala Arg Ala Gly Ala Gly Gln
  1               5                  10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 40

Gly Leu Ala Val Thr Phe Gly Ser Val Leu Glu Gly
  1               5                  10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 41

Val Arg Trp Met Cys Val Ile Arg Leu Gly Val Arg
  1               5                  10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 42

Arg Leu Trp Gly Pro Gly Val Ser Arg Pro Val Leu
  1               5                  10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 43

Cys Gly Ser Ser Leu Phe Arg Gly Pro Arg Cys Pro
  1               5                  10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 44

Leu Gly Ile Ser Ser Leu Ser Phe Leu Gln Leu Arg
```

```
-continued

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 45

Thr Trp Gly Trp Asp Gly Val Ser Tyr Leu Phe Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 46

Thr Arg Ser Leu Phe Asp Asp Phe Val Ser Leu Arg
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 47

Cys Tyr Ala Ser Leu Phe Arg Ser Arg Leu Cys Ala
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 48

Asp Gly Ser Val Arg Val Val Trp Val Arg Leu Leu
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 49

Leu Ser Gly Phe Pro Val Ala Leu Val Arg Phe Ala
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence:Mimotopes
``` and Anti-mimotopes of Human Platelet Glycoprotein Ib/IX

<400> SEQUENCE: 50

Leu Gly Gly Gly Leu Leu Val Gly Ser Val Phe Pro
 1               5                  10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 51

Val Trp Ala Arg Gly Val Phe Arg Asp Arg Phe Phe
 1               5                  10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 52

Thr Gly Leu Leu Ala Gly Pro Val Trp Arg Trp Thr
 1               5                  10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 53

Trp Leu Gly Gly Ile Phe Ser Cys Leu Val Cys Gly
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 54

Trp Phe Leu Arg Asp Val Gly Cys Gly Ser Cys Leu
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 55

Ser Arg Cys Gly Val Phe Thr Trp Cys Ser Arg Ser
 1               5                  10

<210> SEQ ID NO 56

```
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 56

Arg Cys Leu Val Gly Tyr Arg Cys Trp Gly Gly Val
 1               5                  10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 57

Gly Phe Arg Cys Leu Val Met Gly Gly Gly Cys Ala
 1               5                  10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 58

Cys Gly Phe Asp Leu Val Cys Ala Arg Leu Phe Gly
 1               5                  10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 59

Asp Ser Gly Val Arg Trp Phe Phe Gly Phe Leu Gly
 1               5                  10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 60

Ile Leu Asp Gly Cys Phe Phe Leu Gly Arg Cys Pro
 1               5                  10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 61
```

Cys Val Arg Trp Leu Val Ser Ala Gly Cys Ser Gly
 1               5                  10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 62

Cys Val Gly Cys Trp Leu Val Cys Asp Val Leu Leu
 1               5                  10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 63

Cys Leu Phe Val Phe Ala Ala Gly Phe Ala Cys Gly
 1               5                  10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 64

Ser Cys Ala Leu Phe Gly Ser Cys Phe Gly Ile Ser
 1               5                  10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 65

Cys Trp Gly Gly Val Gly Val Cys Gly Leu Leu Val
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 66

Lys Arg Ala Trp Trp Lys Gln Lys Trp Val
 1               5                  10

<210> SEQ ID NO 67
<211> LENGTH: 12
<212> TYPE: PRT
<213> ORGANISM: Artificial Sequence
<220> FEATURE:

```
<223> OTHER INFORMATION: Description of Artificial Sequence:Mimotopes
      and Anti-mimotopes of Human Platelet Glycoprotein Ib/IX

<400> SEQUENCE: 67

Cys Val Gly Gly Val Ala Ser Arg Cys Gly Val Leu
 1               5                  10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 68

Ser Gly Ala Val Leu Ala Gly Pro Phe Gly Val Trp
 1               5                  10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 69

Cys Arg Ala Phe Asp Arg Val Gly Val Cys Val Trp
 1               5                  10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 70

Arg Cys Leu Val Gly Tyr Val Val Gly Gly Val Trp
 1               5                  10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 71

Val Cys Leu Val Tyr Arg Ser Val Asp Cys Trp Ala
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 72

Trp Arg Val Phe Val Phe Thr Cys Val Val Trp Ala
 1               5                  10
```

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 73

Leu Trp Arg Glu Trp Arg Gly Leu Phe Ala Val Leu
 1               5                  10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 74

Ser Gly Ala Val Leu Ala Gly Pro Leu Trp Arg Leu
 1               5                  10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 75

Phe Val Val Arg Gly Gly Thr Phe Leu Phe Val Arg
 1               5                  10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 76

Lys Trp Trp Val Pro Arg His Arg Val Trp
 1               5                  10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 77

Thr Gly Leu Leu Ala Gly Pro Val Trp Arg Trp Thr
 1               5                  10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 78

```
Asp Ser Gly Val Arg Trp Phe Phe Gly Phe Leu Gly
  1               5                  10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 79

Cys Ala Trp His Arg Leu Ser Phe Cys Gly Leu Val
  1               5                  10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 80

Cys Phe Gly Ser Ala Leu Val Leu Ala Val Leu Ala
  1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 81

Trp Phe Trp Asp Met Ser Gly Glu Trp Gly Gly Leu
  1               5                  10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 82

Arg Ser Lys Trp Trp Val His Arg His Ser
  1               5                  10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 83

Arg Ser Lys Trp Trp Val His Arg His Ser
  1               5                  10

<210> SEQ ID NO 84
<211> LENGTH: 10
<212> TYPE: PRT
<213> ORGANISM: Artificial Sequence
```

```
<220> FEATURE:
<223> OTHER INFORMATION: Description of Artificial Sequence:Mimotopes
      and Anti-mimotopes of Human Platelet Glycoprotein Ib/IX

<400> SEQUENCE: 84

His Arg Pro Leu Ser Trp Lys Gly Arg Ala
 1               5                  10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 85

Trp His Arg Arg Pro Met Ser Trp Tyr Ser
 1               5                  10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 86

His Arg Pro Leu Ser Trp Lys Gly Arg Ala
 1               5                  10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 87

Lys Arg Gly Trp His Trp Lys Ser Leu His
 1               5                  10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 88

Lys Lys Ser Trp Trp Val Arg Met Pro Arg
 1               5                  10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 89

Ala Lys Ser Trp Arg Tyr Trp Arg Met Pro
 1               5                  10
```

```
<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 90

Lys Arg Trp Lys Val Tyr His Arg Trp Pro
 1               5                  10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 91

Leu His Arg Trp Lys Gln Ser Pro Arg Thr
 1               5                  10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 92

Leu Ile Arg Trp Lys Pro His Gly Trp Arg
 1               5                  10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 93

Gln Lys Lys Phe Phe Ser Arg Trp Lys His
 1               5                  10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 94

Arg His Val Ala Trp Trp Arg Gln Gly Val
 1               5                  10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX
```

```
-continued

<400> SEQUENCE: 95

Ala Lys His Arg Trp Trp Arg Arg Pro Val
 1               5                  10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 96

Lys His Phe Met Arg His Arg His Gly Val
 1               5                  10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 97

Ala Gly Leu Asn His Trp Trp Lys His Lys
 1               5                  10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 98

Arg Arg Ser Thr Trp His Trp Trp His Ala
 1               5                  10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 99

Val Ala Lys Trp Arg His Trp Asn Arg Gln
 1               5                  10

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 100

Cys Thr Cys Ala Thr Ala Gly Thr Thr Ala Gly Cys Gly Thr Ala Ala
 1               5                  10                  15

Cys Gly

<210> SEQ ID NO 101
```

```
<211> LENGTH: 13
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein
      Ib/IX

<400> SEQUENCE: 101

Glu Asn Val Tyr Val Trp Lys Gln Gly Val Asp Val Lys
  1               5                  10

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 102

Ile Val Leu Arg Cys His Ser Trp Lys Asp Lys Pro Leu Val Lys
  1               5                  10                  15

<210> SEQ ID NO 103
<211> LENGTH: 19
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 103

Asp Asn Ala Glu Asn Val Tyr Val Trp Lys Gln Gly Val Asp Val Lys
  1               5                  10                  15

Ala Met Thr

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein
      Ib/IX

<400> SEQUENCE: 104

Arg His Val Ala Trp Trp Arg Gln Val Val
  1               5                  10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 105

Arg His Val Ala Trp Trp Lys Gln Val Val
  1               5                  10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence:Mimotopes
``` and Anti-mimotopes of Human Platelet Glycoprotein Ib/IX

<400> SEQUENCE: 106

Arg His Val Ala Trp Trp Lys Gln Gly Val
 1               5                  10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 107

Tyr Val Trp Lys Gln Val Val Asp Val Lys
 1               5                  10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 108

Tyr Val Trp Lys Gln Gly Val Asp Val Lys
 1               5                  10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 109

Arg Trp Trp His Trp Val His Arg Glu Thr
 1               5                  10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 110

Lys Arg Trp Leu Trp Trp Ala Asn Pro Arg
 1               5                  10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 111

Lys Arg Trp Leu Trp Trp Ala Asn Pro Arg
 1               5                  10

<210> SEQ ID NO 112

```
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 112

Arg Leu Trp Pro Gln His Arg Gly His Arg
 1               5                  10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 113

Arg Leu Trp Pro Gln His Arg Gly His Arg
 1               5                  10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 114

Lys Arg Trp His Ile Arg Pro Thr Ile Arg
 1               5                  10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 115

Thr Lys Arg Phe Lys His Arg His Phe Leu
 1               5                  10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 116

Ala Lys Trp His Trp His Thr Arg Gly Arg
 1               5                  10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 117
```

Trp His Arg His Trp Gly Gly Phe Arg Ile
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 118

Trp His Arg Asn Lys Pro Thr Trp His Ser
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 119

Trp His Arg Ala Gly Val Arg Ala Lys Val
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 120

Trp His Arg Ala Gly Val Arg Ala Lys Val
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 121

Met Met Ala Trp His Ala Arg Val Ala Arg
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 122

Trp Ile Trp His Arg Pro Ile Lys Val Lys
1               5                   10

<210> SEQ ID NO 123
<211> LENGTH: 10
<212> TYPE: PRT
<213> ORGANISM: Artificial Sequence
<220> FEATURE:

```
<223> OTHER INFORMATION: Description of Artificial Sequence:Mimotopes
      and Anti-mimotopes of Human Platelet Glycoprotein Ib/IX

<400> SEQUENCE: 123

Trp His Arg Thr Leu Pro Lys Arg Gly His
 1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 124

Val Lys His Phe Arg Trp Arg Pro Val Ala
 1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 125

Lys Arg His Trp Arg Phe Gln Leu Ser Asn
 1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 126

Lys Arg His Arg Leu Ala Ser Met Ala Pro
 1               5                   10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 127

Trp Arg Trp Arg Trp Arg Gly Val Leu Arg
 1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 128

Arg Leu His Ala His His Ala Arg His Arg
 1               5                   10
```

```
<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 129

Arg Trp Gly Ala Lys His Arg Val Arg Val
 1               5                  10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 130

Ala Met Gly Trp Arg Pro Val Lys His Arg
 1               5                  10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 131

Lys Trp Arg Trp Arg Met His Gln His Tyr
 1               5                  10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 132

Trp Leu Ser Lys Leu Gly His Arg His Ala
 1               5                  10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 133

Lys His Cys Ser Ile His Thr Arg Leu Arg
 1               5                  10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 134
```

```
Gly Ser Ala Glu Arg Met Ser Glu Gly His
 1               5                  10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 135

Phe Pro Leu Trp Asn Val Leu Thr Met Thr
 1               5                  10

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 136

Ser Phe Ala Gly Val Gly Trp Phe Ala Leu Leu Gly
 1               5                  10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 137

Cys Asp Leu Trp Val Cys Phe Leu Asp Gly Gly Gly
 1               5                  10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 138

Leu Val Ala Arg Phe Pro Pro Tyr Gly Gly Val
 1               5                  10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 139

Ser Ile Val Trp Leu Thr Arg Pro Lys Gly
 1               5                  10

<210> SEQ ID NO 140
<211> LENGTH: 10
<212> TYPE: PRT
<213> ORGANISM: Artificial Sequence
```

```
<220> FEATURE:
<223> OTHER INFORMATION: Description of Artificial Sequence:Mimotopes
      and Anti-mimotopes of Human Platelet Glycoprotein Ib/IX

<400> SEQUENCE: 140

Cys Arg Tyr Arg Ala Leu Asn Gly Val Leu
 1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 141

Ala Leu Thr Ser Arg Thr Trp Ala Arg Gln
 1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 142

Thr Arg Tyr Met Leu Ser Arg Gln Ser Asn
 1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 143

Ala Met Arg Glu Ala Arg Ile Thr Val Lys
 1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 144

Trp Arg Arg His Val Pro Leu Arg Ile Leu
 1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 145

Phe His Arg Trp Asn Arg Pro Met Val Thr
 1               5                   10
```

```
<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 146

His Arg Tyr Lys Lys Thr Pro Val Pro Met
 1               5                  10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 147

Trp Leu His Val Lys Arg Arg Pro Val Val
 1               5                  10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 148

Trp Val Arg His Lys His Pro Ile Val Pro
 1               5                  10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 149

Leu Ser Met Arg Arg Arg Gln Phe Gln Ser
 1               5                  10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 150

Phe His Trp Arg Asp Lys Trp Arg Thr Gly
 1               5                  10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX
```

```
<400> SEQUENCE: 151

Arg Met Arg Arg Pro Gly Ile Thr Val Lys
 1               5                  10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 152

Gly His Arg Trp Asn Arg Pro Met Val Thr
 1               5                  10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 153

Trp His Arg His Thr Pro Lys Arg Ile Pro
 1               5                  10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 154

Trp His Trp Gln Arg Ser Arg Pro Ala Leu
 1               5                  10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 155

Trp His Trp Gln Arg Ser Arg Pro Ala Leu
 1               5                  10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 156

Lys Arg Trp Arg His Ser Leu Pro Ala Ser
 1               5                  10

<210> SEQ ID NO 157
<211> LENGTH: 10
<212> TYPE: PRT
```

<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 157

Lys Arg Trp Arg His Ser Leu Pro Ala Ser
 1               5                  10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 158

Lys Lys Trp Gly Gln His Arg Gln Arg Ser
 1               5                  10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 159

Trp Arg Trp Met His Trp Met Pro His Ala
 1               5                  10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 160

Trp His Trp Leu Ala Arg His Arg Thr Val
 1               5                  10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 161

Arg His Arg His Arg Gly Phe Gln Pro Arg
 1               5                  10

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence:Mimotopes
and Anti-mimotopes of Human Platelet Glycoprotein Ib/IX

<400> SEQUENCE: 162

Arg Gly Trp Arg Trp His Lys Tyr Trp Gln
 1               5                  10

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 163

Lys Arg His Ala Trp Met Lys Ser Arg Leu
 1               5                  10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 164

Leu Leu Leu Val Gly Gly Ser Glu Leu Thr
 1               5                  10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 165

Lys Lys Val Trp Met Phe Ser Tyr Asn Glu
 1               5                  10

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 166

Leu Ser Cys Arg Gly Cys Arg Ala Phe Val
 1               5                  10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 167

His Glu Gly Cys Glu Ala Gln Asp Glu Leu
 1               5                  10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

```
<400> SEQUENCE: 168

Ser Val Arg His Ile Trp Phe His Val Lys
 1               5                  10

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 169

Gly Thr Trp Asp Leu Trp Arg Lys Gly Ser
 1               5                  10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 170

Arg Trp Leu Trp Pro Arg Val His Lys Thr
 1               5                  10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 171

His Ser Pro Phe Arg His Val Gln Pro Arg
 1               5                  10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 172

Trp Val Arg Gly His His Arg Glu Val Arg
 1               5                  10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX

<400> SEQUENCE: 173

Glu Asn Val Tyr Val Trp Lys Gln Gly Val
 1               5                  10

<210> SEQ ID NO 174
<211> LENGTH: 6
```

```
                                  -continued
<212> TYPE: PRT
<213> ORGANISM: Artificial Sequence
<220> FEATURE:
<223> OTHER INFORMATION: Description of Artificial Sequence:Mimotopes
      and Anti-mimotopes of Human Platelet Glycoprotein Ib/IX
<220> FEATURE:
<221> NAME/KEY: SITE
<222> LOCATION: (3)..(4)
<223> OTHER INFORMATION: variable amino acid

<400> SEQUENCE: 174

Trp Arg Xaa Xaa Glu Tyr
  1               5
```

MIMOTOPES AND ANTI-MIMOTOPES OF HUMAN PLATELET GLYCOPROTEIN IB/IX

This application is a divisional of U.S. Ser. No. 09/258,947, filed Mar. 1, 1999 now U.S. Pat. No. 7,074,888 which was a continuation-in-part of U.S. Ser. No. 08/556,597, filed Nov. 13, 1995 (U.S. Pat. No. 5,877,155, issued Mar. 2, 1999) which was a continuation-in-part of U.S. Ser. No. 08/406,330, filed Mar. 17, 1995 (U.S. Pat. No. 5,817,748, issued Oct. 6, 1998), the contents of each of which are hereby incorporated by reference.

FIELD OF THE INVENTION

The present invention relates to a peptide capable of functionally mimicking the binding site for a monoclonal antibody (i.e. a mimotope), the monoclonal antibody recognizing an epitope within the human platelet glycoprotein Ib/IX complex, and to isolated molecules capable of binding to the peptide (i.e. an anti-mimotope).

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The platelet glycoprotein Ib/IX (GPIb/IX) receptor for von Willebrand factor (vWf) is believed to consist of a 1:1 heterodimeric complex (Du et al. 1987) between GPIb (160 kDa) and GPIX (17 kDa) in a noncovalent association. GPIb in turn consists of a disulfide-linked 140 kDa alpha chain (GPIb alpha) and a 22 kDa beta chain (GPIb beta) (Fitzgerald and Phillips 1989).

The GPIb/IX complex comprises one of the major transmembrane receptor complexes on blood platelets (Roth 1991; Lopez 1994; Clemetson and Clemetson 1995), mediating von Willebrand factor (vWF)-dependent platelet adhesion. The human autosomal dominant bleeding disorder termed platelet-type von Willebrand disease (PT-vWD) represents a naturally occurring model of an up-regulated GPIb/IX receptor (Miller and Castella 1982; Miller et al. 1983). In this disorder, abnormally low concentrations of the chemical modulator ristocetin are able to promote the interaction of vWF with GPIb/IX. Additionally, the platelets from such patients are aggregated at a lower shear force than required for normal platelets (Murata et al. 1993). One kindred of PT-vWD patients was found to have a single point mutation leading to a substitution of valine for glycine at residue 233 of the GPIb alpha chain (Miller et al. 1991). A second point mutation in very close proximity (substitution of valine for methionine at residue 239 (Russell and Roth 1993; Takahashi et al 1995) has been described in two additional kindreds displaying the PT-vWD phenotype (Weiss et al. 1982; Takahashi 1980).

In the 1980's, Miller et al. developed a series of monoclonal antibodies (mab) directed against the GP Ib/IX complex receptor for vWf. In particular, monoclonal antibody C-34 was characterized in detail and it was determined that mab C-34 recognized an epitope within the platelet glycoprotein Ib/IX complex (Miller et al. 1990). In this and subsequent work, Miller et al. showed that monoclonal antibodies C-34, AS-2 and AS-7 were potent inhibitors of the ristocetin-induced aggregation of normal platelets that was dependent upon von Willebrand factor. Miller et al. also showed that the epitopes for all three monoclonal antibodies lay within the GPIb/IX complex. Miller et al. were able to localize monoclonal antibody binding sites for AS-2 and AS-7 to the amino-terminal 45 kDa of GPIb alpha. The epitope for C-34 was recently localized to the extracellular portion of the GPIb alpha chain expressed on the surface of Chinese Hamster Ovary cells (Chambers et al. 1995). The failure of C-34 to bind to denatured GPIb alpha in Western blots (Ward and Berndt 1995; Clemetson and Hugli 1995), or to immunoprecipitate the extracellular region of GPIb alpha removed from platelets under a variety of experimental conditions (Miller et al. 1990) strongly suggests that the epitope recognized by C-34 is highly conformation-dependent. Recently Ward and Berndt have, however, now reported the successful immunoprecipitation by C-34 of a 1.His-Arg.293 amino-terminal fragment of $^{125}$I-labeled glycocalicin following digestion of the purified molecule by trypsin (Ward and Berndt 1995).

Attempts to define the binding sites for various monoclonal antibodies have led to the development of epitope libraries. Parmley and Smith developed a bacteriophage expression vector that could display foreign epitopes on its surface (Parmley and Smith 1988). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley and Smith 1988; Cwirla et al. 1990; Scott and Smith 1990; Christian et al. 1992; Smith and Scott 1993).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley and Smith 1988; Scott 1992).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found. LaRocca et al. (1992) expressed a mimotope of the human breast epithelial mucin tandem repeat in *Escherichia coli*. Balass et al. (1993) identified a hexapeptide that mimics a conformation-dependent binding site of the acetylcholine receptor. Hobart et al. (1993) isolated a mimotope that mimics the C6 epitope (the epitope for the sixth component of complement).

The sequences of these mimotopes, by definition, do not identify a continuous linear native sequence or necessarily occur in any way in a naturally-occurring molecule, i.e. a naturally occuring protein. The sequences of the mimotopes merely form a peptide which functionally mimics a binding site on a naturally-occurring protein. For example, the mimotope of Balass et al. (1993) mimics the binding site of the acetylcholine receptor.

Many of these mimotopes are short peptides. The availability of short peptides which can be readily synthesized in large amounts and which can mimic naturally-occurring sequences (i.e. binding sites) offers great potential application.

A need continues to exist, therefore, for the elucidation of useful mimotopes.

SUMMARY OF INVENTION

This need is met by the mimotopes of the subject invention. The invention thus provides an isolated peptide that functionally mimics a binding site for a monoclonal antibody, the monoclonal antibody recognizing an epitope within the human platelet glycoprotein Ib/IX complex. This isolated peptide is a mimotope. A peptide functionally mimics a binding site for a monoclonal antibody if the monoclonal antibody can bind to the peptide. Preferably, the isolated peptide comprises an amino acid sequence as shown in SEQ ID NO:174: WRXXEY.

The invention further provides an isolated molecule capable of binding to the peptide, which molecule can be an antibody, a second peptide, a carbohydrate, a DNA molecule, an RNA molecule, or any chemically synthesized molecule, for example. This isolated molecule is an anti-mimotope. Anti-mimotopes that bind to a receptor can be used to mediate the functional activity of that receptor. Preferably, the isolated molecule is capable of binding to the isolated peptide described above (the isolated peptide that comprises an amino acid sequence as shown in SEQ ID NO:174). This preferred isolated molecule inhibits ristocetin induced aggregation of platelets and has a three dimensional structure complementary to the three dimensional structure of the isolated peptide.

The invention also provides a method for modulating the adhesion, aggregation, or agglutination of platelets, each of which is dependent on von Willebrand factor interaction with platelets through the glycoprotein Ib/IX complex receptor. The methods provide for exposure of platelets to the molecule (anti-mimotope) in order to modulate adhesion, aggregation, or agglutination of the platelets.

The invention further provides a method of identifying a molecule that inhibits ristocetin induced aggregation of platelets. The method comprises determining whether a molecule binds to the isolated peptide described above (the isolated peptide that comprises an amino acid sequence as shown in SEQ ID NO:174), and screening a molecule that binds to the peptide to determine whether the screened molecule inhibits ristocetin induced aggregation of platelets.

The invention further provides an isolated peptide capable of binding to monoclonal antibody C-34, as well as an isolated molecule capable of binding to such peptide. Also provided is a method for modulating the adhesion, aggregation, or agglutination of platelets by exposing the platelets to the molecule (anti-mimotope).

In a preferred embodiment, the isolated peptide capable of binding to monoclonal antibody C-34 includes an amino acid sequence corresponding to SEQ ID NO:38: WNWRYREYV.

The invention still further provides an isolated peptide capable of binding to monoclonal antibody SZ-2, as well as an isolated molecule capable of binding to such peptide. Also provided is a method for modulating the adhesion, aggregation, or agglutination of platelets by exposing the platelets to the molecule (anti-mimotope).

BRIEF DESCRIPTION OF THE DRAWINGS

These and other features and advantages of this invention will be evident from the following detailed description of preferred embodiments when read in conjunction with the accompanying drawings in which:

FIG. 1 illustrates the ristocetin-induced full aggregation of platelets in the presence of von Willebrand factor;

FIG. 2 illustrates the inhibition of ristocetin-induced aggregation of platelets by 20 μg/ml of monoclonal antibody C-34;

FIG. 3 illustrates the continued inhibition of ristocetin-induced aggregation of platelets by 20 μg/ml of mab C-34 in the presence of 0.14 μM of the synthetic peptide mimotope having SEQ ID NO: 1: AWNWRYREYV;

FIG. 4 illustrates the partial neutralization of the inhibition of ristocetin-induced aggregation of platelets by 20 μg/ml of mab C-34 in the presence of 0.27 μM of the synthetic peptide mimotope having SEQ ID NO: 1: AWNWRYREYV;

FIG. 5 illustrates the partial neutralization of the inhibition of ristocetin-induced aggregation of platelets by 20 μg/ml of mab C-34 in the presence of 0.55 μM of the synthetic peptide mimotope having SEQ ID NO: 1: AWNWRYREYV;

FIG. 6 illustrates the partial neutralization of the inhibition of ristocetin-induced aggregation of platelets by 20 μg/ml of mab C-34 in the presence of 1.1 μM of the synthetic peptide mimotope having SEQ ID NO: 1: AWNWRYREYV;

FIG. 7 illustrates the complete neutralization of the inhibition of ristocetin-induced aggregation of platelets by 20 μg/ml of mab C-34 in the presence of 2.3 μM of the synthetic peptide mimotope having SEQ ID NO: 1: AWNWRYREYV;

FIG. 8 illustrates the functional screening of candidate anti-mimotope bacteriophage clones. Following incubation of 150 μL of the indicated bacteriophage clones with 250 μL of citrated PRP for 1 hr at 22° C., aggregation was initiated by the addition of 0.8 mg/mL ristocetin under stirring conditions at 37° C.;

DETAILED DESCRIPTION

Figure 9:
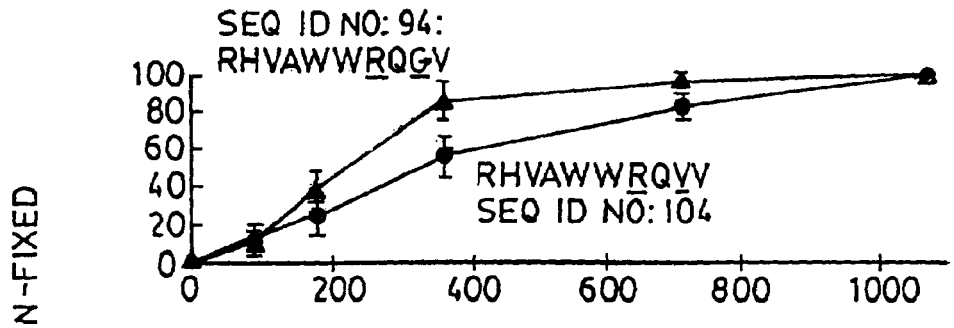
FIGS. 9-11 illustrate the effect of synthetic peptides upon ristocetin-induced aggregation of formalin-fixed platelets.

The invention provides an isolated peptide that functionally mimics a binding site for a monoclonal antibody, the monoclonal antibody recognizing an epitope within the human glycoprotein Ib/IX complex. This peptide is called a mimotope.

In one preferred embodiment, the monoclonal antibody is designated C-34, and the peptide includes an amino acid sequence selected from the group consisting of:
SEQ ID NO:1: AWNWRYREYV
SEQ ID NO:2: KWNWRNKKYV
SEQ ID NO:3: LSTWRYFEYV
SEQ ID NO:4: YLGWRYSEYV
SEQ ID NO:5: TQMWRAREYL
SEQ ID NO:6: WRQREYWDPV
SEQ ID NO:7: EGSWRYRKGG
SEQ ID NO:8: GYHWWRNWEY
SEQ ID NO:9: KGFLWRARNW
SEQ ID NO:10: MNWKHWRARH
SEQ ID NO:11:FKWREWRGKL
SEQ ID NO:12:PDRQVRLWVR
SEQ ID NO:13:RVLRHWHPRT
SEQ ID NO:14:GRRVWMLNHG
SEQ ID NO:15:KKGRHHVTRV
SEQ ID NO:16: GGVCKCWQCL
SEQ ID NO:17: FSHSYGSAIR
SEQ ID NO:18: MHGHRRPGLA
SEQ ID NO:19: MSKKPHLGLR
SEQ ID NO:20: TMWVELYSLK
SEQ ID NO:21: FVDPGRAGRG SEQ ID NO:23: FRCCVFSCCLLS
SEQ ID NO:24: GFRCLVSLGGCF
SEQ ID NO:25: YSLWGLPVGDVV
SEQ ID NO:26: LPLLWFNGAGFF
SEQ ID NO:27: VWGLFRGLENGS
SEQ ID NO:28: SLWRQWRGLFVV
SEQ ID NO:29: TLSLFGGRDKGF
SEQ ID NO:30: IGPAVSCLFRVC
SEQ ID NO:31: MSLFPLSFCRLI
SEQ ID NO:32: ALFSSVWGDVTL
SEQ ID NO:33: GWFGPFWVRGSG
SEQ ID NO:34: FWVSVGGVEGVV
SEQ ID NO:35: LGAFGGAGFLWR
SEQ ID NO:36: CRGIVFLFVGWL
SEQ ID NO:37: FWLVKGAGAWRF
SEQ ID NO:39: QVRLWARAGAGQ
SEQ ID NO:40: GLAVTFGSVLEG
SEQ ID NO:41: VRWMCVIRLGVR
SEQ ID NO:42: RLWGPGVSRPVL
SEQ ID NO:43: CGSSLFRGPRCP
SEQ ID NO:44: LGISSLSFLQLR
SEQ ID NO:45: TWGWDGVSYLFL
SEQ ID NO:46: TRSLFDDFVSLR
SEQ ID NO:47: CYASLFRSRLCA
SEQ ID NO:48: DGSVRVVWVRLL
SEQ ID NO:49: LSGFPVALVRFA
SEQ ID NO:50: LGGGLLVGSVFP
SEQ ID NO:51: VWARGVFRDRFF
SEQ ID NO:52: TGLLAGPVWRWT
SEQ ID NO:53: WLGGIFSCLVCG
SEQ ID NO:54: WFLRDVGCGSCL
SEQ ID NO:55: SRCGVFTWCSRS
SEQ ID NO:56: RCLVGYRCWGGV
SEQ ID NO:57: GFRCLVMGGGCA
SEQ ID NO:58: CGFDLVCARLFG
SEQ ID NO:59: DSGVRWFFGFLG
SEQ ID NO:60: ILDGCFFLGRCP
SEQ ID NO:61: CVRWLVSAGCSG
SEQ ID NO:62: CVGCWLVCDVLL
SEQ ID NO:63: CLFVFAAGFACG
SEQ ID NO:64: SCALFGSCFGIS
SEQ ID NO:65: CWGGVGVCGLLV
SEQ ID NO:66: KRAWWKQKWV
SEQ ID NO:67: CVGGVASRCGVL
SEQ ID NO:68: SGAVLAGPFGVW
SEQ ID NO:69: CRAFDRVGCVW
SEQ ID NO:70: RCLVVGYVVGGVW
SEQ ID NO:71: VCLVYRSVDCWA
SEQ ID NO:72: WRVFVFTCVVWA
SEQ ID NO:73: LWREWRGLFAVL
SEQ ID NO:74: SGAVLAGPLWRL
SEQ ID NO:75: FVVRGGTFLFVR
SEQ ID NO:77: TGLLAGPVWRWT
SEQ ID NO:78: DSGVRWFFGFLG
SEQ ID NO:79: CAWHRLSFCGLV
SEQ ID NO:80: CFGSALVLAVLA and
SEQ ID NO:81: WFWDMSGEWGGL.

Preferably, the peptide includes an amino acid sequence corresponding to consensus sequence SEQ ID NO: 38: WNWRYREYV.

In a presently preferred embodiment, the isolated peptide comprises an amino acid sequence as shown in SEQ ID NO:174: WRXXEY. This consensus sequence is derived from the epitope mapping studies of mab C-34 as discussed below (see series of cloned sequences included in alignment form). Amino acid residue number 3 of SEQ ID NO:174 is preferably selected from the group consisting of alanine, asparagine, glutamine, and tyrosine. Amino acid residue number 4 of SEQ ID NO:174 is preferably selected from the group consisting of arginine, phenylalanine, serine, and tryptophan.

Each of these peptides, represented by SEQ ID NOs 1 to 21, 23-37, 39-75, 77-81, and 174 mimics the binding site within GPIb/IX for mab C-34. Mab C-34 thus binds to each of these peptides. However, the sequences of each of these peptides do not identify a continuous linear native sequence or necessarily occur at all within the sequence of any chain (i.e. GPIb alpha, GPIb beta, GPIX) of the GPIb/IX complex, thus the peptides are mimicking the mab C-34 binding site and are therefore mimotopes. The peptide of the subject invention also includes fragments of the above exemplified peptides which retain the ability to functionally mimic the binding site for a monoclonal antibody, such as C-34. The peptide having an amino acid sequence corresponding to SEQ ID NO:38 is an example of such a fragment, being a fragment of the peptide which includes the amino acid sequence corresponding to SEQ ID NO:1.

In another embodiment, the monoclonal antibody is designated SZ-2, and the peptide includes an amino acid sequence selected from the group consisting of:

SEQ ID NO:83: WHWRSSWKSG
SEQ ID NO:84: HRPLSWKGRA
SEQ ID NO:85: WHRRPMSWYS
SEQ ID NO:86: ARIKIWKPRW
SEQ ID NO:87: KRGWHWKSLH
SEQ ID NO:88: KKSWWVRMPR
SEQ ID NO:89: AKSWRYWRMP
SEQ ID NO:90: KRWKVYHRWP
SEQ ID NO:91: LHRWKQSPRT
SEQ ID NO:92: LIRWKPHGWR
SEQ ID NO:93: QKKFFSRWKH
SEQ ID NO:76: KWWVPRHRVW
SEQ ID NO:82: RSKWWVHRHS
SEQ ID NO:109:RWWHWVHRET
SEQ ID NO:110: KRWLWWANPR
SEQ ID NO:111: RHLWWGGRMK
SEQ ID NO:112: RLWPQHRGHR
SEQ ID NO:113: KRWHIRPTIR
SEQ ID NO:114: KRFKTHVHGR
SEQ ID NO:115: TKRFKHRHFL
SEQ ID NO:116: AKWHWHTRGR
SEQ ID NO:117: WHRHWGGFRI
SEQ ID NO:118: WHRNKPTWHS
SEQ ID NO:119: WHRAGVRAKV
SEQ ID NO:120: FKRFWHTGHR
SEQ ID NO:121: MMAWHARVAR
SEQ ID NO:122: WIWHRPIKVK
SEQ ID NO:123: WHRTLPKRGH
SEQ ID NO:124: VKHFRWRPVA
SEQ ID NO:125: KRHWRFQLSN
SEQ ID NO:126: KRHRLASMAP
SEQ ID NO:127: WRWRWRGVLR
SEQ ID NO:128: RLHAHHARHR
SEQ ID NO:129: RWGAKHRVRV
SEQ ID NO:130: AMGWRPVKHR
SEQ ID NO:131: KWRWRMHQHY
SEQ ID NO:132: WLSKLGHRHA
SEQ ID NO:133: KHCSIHTRLR
SEQ ID NO:134: GSAERMSEGH
SEQ ID NO:135: FPLWNVLTMT
SEQ ID NO:136: SFAGVGWFALLG
SEQ ID NO:137: CDLWVCFLDGGG
SEQ ID NO:138: LVARFPPPYGGV
SEQ ID NO:139: SIVWLTRPKG

SEQ ID NO:140: CRYRALNGVL
SEQ ID NO:141: ALTSRTWARQ
SEQ ID NO:142: TRYMLSRQSN
SEQ ID NO:143: AMREARITVK
SEQ ID NO:144: WRRHVPLRIL
SEQ ID NO:145: FHRWNRPMVT
SEQ ID NO:146: HRYKKTPVPM
SEQ ID NO:147: WLHVKRRPVV
SEQ ID NO:148: WVRHKHPIVP
SEQ ID NO:149: LSMRRRQFQS
SEQ ID NO:150: FHWRDKWRTG
SEQ ID NO:151: RMRRPGITVK
SEQ ID NO:152: GHRWNRPMVT
SEQ ID NO:153: WHRHTPKRIP
SEQ ID NO:154: WHWQRSRPAL
SEQ ID NO:155: KRTWWHYIRP and
SEQ ID NO:156: KRWRHSLPAS.

Each of these peptides, represented by SEQ ID NOs 83-93, 76, 82, and 109-156, mimics the binding site within GPIb/IX for mab SZ-2. Mab SZ-2 thus binds to each of these peptides, which are referred to as mimotopes. The peptide of the subject invention also includes fragments of the above exemplified peptides which retain the ability to functionally mimic the binding site for monoclonal antibody SZ-2.

As used herein, a "peptide" refers to an amino acid sequence of three to one hundred amino acids, and therefore an isolated peptide that comprises an amino acid sequence is not intended to cover amino acid sequences of greater than 100 amino acids. Preferably, the peptides of the subject invention (whether they be mimotope or anti-mimotope peptides) are less than 50 amino acids in length, and more preferably the peptides are five to 20 amino acids in length or 20-40 amino acids in length.

The peptides described herein can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptides of the present invention depends, in part, on the desired characteristics of the peptide. For example, the incorporation of one or more (D)-amino acids can confer increased stability on the peptide and can allow a peptide to remain active in the body for an extended period of time. The incorporation of one or more (D)-amino acids can also increase or decrease the pharmacological activity of the peptide.

The peptides may also be cyclized, since cyclization may provide the peptides of the present invention with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC, 46: 257 (1981) and Raucher et al., Tetrahedron. Lett., 21: 14061 (1980). An amino acid mimic is, therefor, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual peptide based on the modifications to the backbone or side chain functionalities. For example, these types of alterations to the specifically described amino acid substituents and exemplified peptides can enhance the peptide's stability to enzymatic breakdown and increase biological activity. Modifications to the peptide backbone similarly can add stability and enhance activity.

One skilled in the art, using the above sequences or formulae, can easily synthesize the peptides of this invention. Standard procedures for preparing synthetic peptides are well known in the art. The novel peptides can be synthesized using: the solid phase peptide synthesis (SPPS) method of Merrifield (J. Am. Chem. Soc., 85: 2149 (1964)) or modifications of SPPS; or, the peptides can be synthesized using standard solution methods well known in the art (see, for example, Bodanzsky, M., Principles of Peptide Synthesis, 2nd revised ed., Springer-Verlag (1988 and 1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82: 5131 (1985).

According to the subject invention, the monoclonal antibody (whose binding site is mimicked by the peptide of the invention, i.e. C-34 or SZ-2) recognizes an epitope within the human glycoprotein Ib/IX complex.

The invention also provides an isolated molecule capable of binding to the peptide. This isolated molecule is called an anti-mimotope. The anti-mimotope molecule can be any suitable molecule, such as, for example, an antibody, a second peptide, a carbohydrate, a DNA molecule, an RNA molecule, or a chemically synthesized molecule. Such peptides, proteins, or other biological, synthetic, or semi-synthetic molecules that are capable of binding to the mimotope can be identified by: raising antibodies against the mimotope; selecting from bacteriophage, chemical, hybridoma cell, or other types of libraries, cells, or chemical syntheses that might produce a set or subset of molecules having high affinity for the mimotope sequence; or designing molecules intended to have a high affinity for the mimotope sequences using computer-assisted or other theoretical approaches. Suitable anti-mimotopes can also be developed using in vitro evolution of nucleic acids capable of binding to the peptide mimotope (see Joyce 1994).

In one embodiment, the anti-mimotope of the subject invention constitutes a peptide which includes an amino acid sequence selected from the group consisting of:

SEQ ID NO:94: RHVAWWRQGV
SEQ ID NO:95: AKHRWWRRPV

SEQ ID NO:96: KHFMRHRHGV
SEQ ID NO:97: AGLNHWWKHK
SEQ ID NO:98: RRSTWHWWHA
SEQ ID NO:99: VAKWRHWNRQ
SEQ ID NO:157: AYGVRHLGLS
SEQ ID NO:158: KKWGQHRQRS
SEQ ID NO:159: WRWMHWMPHA
SEQ ID NO:160: WHWLARHRTV
SEQ ID NO:161: RHRHRGFQPR
SEQ ID NO:162: RGWRWHKYWQ
SEQ ID NO:163: KRHAWMKSRL
SEQ ID NO:164: LLLVGGSELT
SEQ ID NO:165: KKVWMFSYNE
SEQ ID NO:166: LSCRGCRAFV
SEQ ID NO:167: HEGCEAQDEL
SEQ ID NO:168: SVRHIWFHVK
SEQ ID NO:169: GTWDLWRKGS
SEQ ID NO:170: RWLWPRVHKT
SEQ ID NO:171: HSPFRHVQPR and
SEQ ID NO:172: WVRGHHREVR.

These particular anti-mimotope peptides were generated to the mimotope which mimics the binding site for monoclonal antibody C-34.

Such anti-mimotopes could serve as anti-thrombotic drugs. For example, the binding of mab C-34 to GPIb/IX inhibits ristocetin-induced aggregation of platelets. The mimotope peptide mimics the binding site in GPIb/IX, and the anti-mimotope molecules bind to the mimotope peptide. Therefore, the anti-mimotopes, which could be peptides, should themselves complement the mimotope peptide. As such, the anti-mimotopes should be capable of binding to the original epitope for mab C-34 or mab SZ-2 within the platelet glycoprotein Ib/IX complex, thereby inducing similar effects as does mab C-34 or mab SZ-2, i.e. the inhibition of ristocetin-induced aggregation of platelets that is dependent upon von Willebrand factor.

The invention thus provides a method of modulating the adhesion, aggregation, or agglutination of platelets, the method comprising selecting platelets and exposing the platelets to the anti-mimotope molecule of the subject invention. Such exposure affects von Willebrand factor interaction with platelets through the glycoprotein Ib/IX receptor, thereby modulating the adhesion, aggregation, or agglutination of the platelets.

The invention also provides an isolated peptide capable of binding to monoclonal antibody C-34, the peptide including an amino acid sequence selected from the group consisting of:

SEQ ID NO:1: AWNWRYREYV
SEQ ID NO:2: KWNWRNKKYV
SEQ ID NO:3: LSTWRYFEYV
SEQ ID NO:4: YLGWRYSEYV
SEQ ID NO:5: TQMWRAREYL
SEQ ID NO:6: WRQRETWDPV
SEQ ID NO:7: EGSWRYRKGG
SEQ ID NO:8: GYHWWRNWEY
SEQ ID NO:9: KGFLWRARNW
SEQ ID NO:10:MNWKHWRARH
SEQ ID NO:11: FKWREWRGKL
SEQ ID NO:12: PDRQVRLWVR
SEQ ID NO:13: RVLRHWHPRT
SEQ ID NO:14: GRRVWMLNHG
SEQ ID NO:15: KKGRHHVTRV
SEQ ID NO:16: GGVCKCWQCL
SEQ ID NO:17: FSHSYGSAIR
SEQ ID NO:18: MHGHRRPGLA
SEQ ID NO:19: MSKKPHLGLR
SEQ ID NO:20: TMWVELYSLK
SEQ ID NO:21: FVDPGRAGRG
SEQ ID NO:23: FRCCVFSCCLLS
SEQ ID NO:24: GFRCLVSLGGCF
SEQ ID NO:25: YSLWGLPVGDVV
SEQ ID NO:26: LPLLWFNGAGFF
SEQ ID NO:27: VWGLFRGLENGS
SEQ ID NO:28: SLWRQWRGLFVV
SEQ ID NO:29: TLSLFGGRDKGF
SEQ ID NO:30: IGPAVSCLFRVC
SEQ ID NO:31: MSLFPLSFCRLI
SEQ ID NO:32: ALFSSVWGDVTL
SEQ ID NO:33: GWFGPFWVRGSG
SEQ ID NO:34: FWVSVGGVEGVV
SEQ ID NO:35: LGAFGGAGFLWR
SEQ ID NO:36: CRGIVFLFVGWL
SEQ ID NO:37: FWLVKGAGAWRF
SEQ ID NO:39: QVRLWARAGAGQ
SEQ ID NO:40: GLAVTFGSVLEG
SEQ ID NO:41: VRWMCVIRLGVR
SEQ ID NO:42: RLWGPGVSRPVL
SEQ ID NO:43: CGSSLFRGPRCP
SEQ ID NO:44: LGISSLSFLQLR
SEQ ID NO:45: TWGWDGVSYLFL
SEQ ID NO:46: TRSLFDDFVSLR
SEQ ID NO:47: CYASLFRSRLCA
SEQ ID NO:48: DGSVRVVWVRLL
SEQ ID NO:49: LSGFPVALVRFA
SEQ ID NO:50: LGGGLLVGSFP
SEQ ID NO:51: VWARGVFRDRFF
SEQ ID NO:52: TGLLAGPVWRWT
SEQ ID NO:53: WLGGIFSCLVCG
SEQ ID NO:54: WFLRDVGCGSCL
SEQ ID NO:55: SRCGVFTWCSRS
SEQ ID NO:56: RCLVGYRCWGGV
SEQ ID NO:57: GFRCLVMGGGCA
SEQ ID NO:58: CGFDLVCARLFG
SEQ ID NO:59: DSGVRWFFGFLG
SEQ ID NO:60: ILDGCFFLGRCP
SEQ ID NO:61: CVRWLVSAGCSG
SEQ ID NO:62: CVGCWLVCDVLL
SEQ ID NO:63: CLFVFAAGFACG
SEQ ID NO:64: SCALFGSCFGIS
SEQ ID NO:65: CWGGVGVCGLLV
SEQ ID NO:66: KRAWWKQKWV
SEQ ID NO:67: CVGGVASRCGVL
SEQ ID NO:68: SGAVLAGPFGVW
SEQ ID NO:69: CRAFDRVGVCVW
SEQ ID NO:70: RCLVGYVVGGVW
SEQ ID NO:71: VCLVYRSVDCWA
SEQ ID NO:72: WRVFVFTCVVWA
SEQ ID NO:73: LWREWRGLFAVL
SEQ ID NO:74: SGAVLAGPLWRL
SEQ ID NO:75: FVVRGGTFLFVR
SEQ ID NO:77: TGLLAGPVWRWT
SEQ ID NO:78: DSGVRWFFGFLG
SEQ ID NO:79: CAWHRLSFCGLV
SEQ ID NO:80: CFGSALVLAVLA and
SEQ ID NO:81: WFWDMSGEWGGL.

Further provided is a fragment of any of the above peptides wherein the fragment retains the ability to bind to monoclonal antibody C-34. Such a fragment is exemplified by SEQ ID NO:38, which is a fragment of SEQ ID NO:1.

The invention also provides an isolated molecule capable of binding to the above peptides, also known as an anti-mimotope. Suitable molecules include an antibody, another peptide, a DNA or RNA molecule, a carbohydrate, or a chemically synthesized molecule.

Figure 12A:
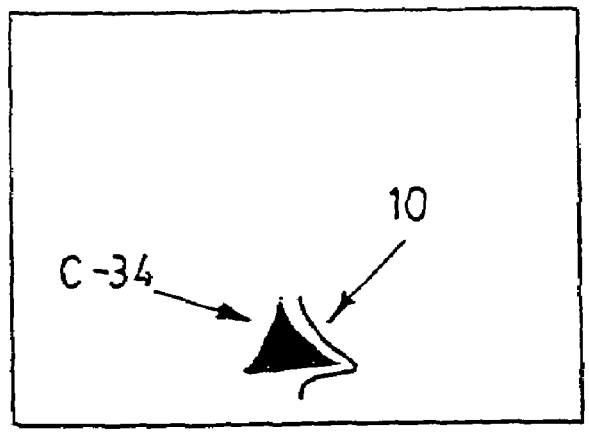
FIGS. 12a-12c are a diagrammatic sketch of mimotopes and anti-mimotopes used to probe the structural relationships in platelet glycoprotein Ib alpha.
Figure 12B:
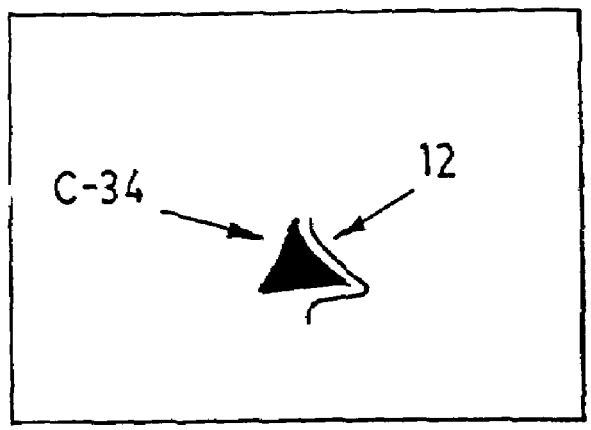
Figure 12C:
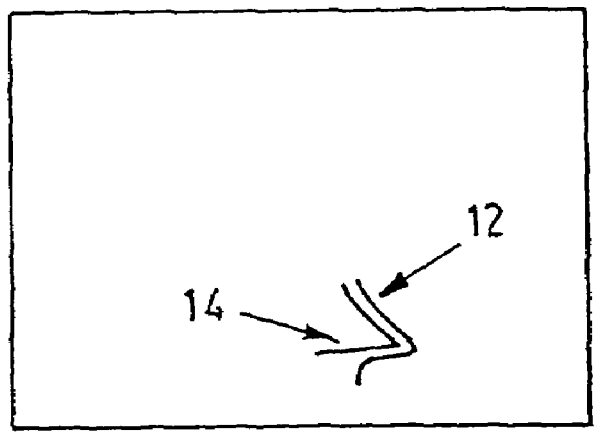

Preferably, the anti-mimotope is an isolated molecule capable of binding to an isolated peptide, wherein the isolated peptide comprises an amino acid sequence as shown in SEQ ID NO:174. This isolated molecule inhibits ristocetin induced aggregation of platelets and has a three dimensional structure complementary to the three dimensional structure of the isolated peptide (comprising an amino acid sequence as shown in SEQ ID NO:174). The concept of "complementary" is illustrated in FIG. 12a-12c.

The invention provides a method of modulating the adhesion, aggregation, or agglutination of platelets, the method comprising selecting platelets and exposing the platelets to the anti-mimotope molecule. Such exposure affects von Willebrand factor interaction with platelets through the glycoprotein Ib/IX receptor, thereby modulating the adhesion, aggregation, or agglutination of the platelets.

In one preferred embodiment, the invention provides an isolated peptide capable of binding to monoclonal antibody C-34 and including an amino acid sequence corresponding to SEQ ID NO:38: WNWRYREYV.

The invention further provides an isolated peptide capable of binding to monoclonal antibody SZ-2, the peptide including an amino acid sequence selected from the group consisting of:
SEQ ID NO:83: WHWRSSWKSG
SEQ ID NO:84: HRPLSWKGRA
SEQ ID NO:85: WHRRPMSWYS
SEQ ID NO:86: ARIKIWKPRW
SEQ ID NO:87: KRGWHWKSLH
SEQ ID NO:88: KKSWWVRMPR
SEQ ID NO:89: AKSWRYWRMP
SEQ ID NO:90: KRWKVYHRWP
SEQ ID NO:91: LHRWKQSPRT
SEQ ID NO:92: LIRWKPHGWR
SEQ ID NO:93: QKKFFSRWKH
SEQ ID NO:76: KWWVPRHRVW
SEQ ID NO:82: RSKWWVHRHS
SEQ ID NO:109: RWWHWVHRET
SEQ ID NO:110: KRWLWWANPR
SEQ ID NO:111: RHLWWGGRMK
SEQ ID NO:112: RLWPQHRGHR
SEQ ID NO:113: KRWHIRPTIR
SEQ ID NO:114: KRFKTHVHGR
SEQ ID NO:115: TKRFKHRHFL
SEQ ID NO:116: AKWHWHTRGR
SEQ ID NO:117: WHRHWGGFRI
SEQ ID NO:118: WHRNKPTWHS
SEQ ID NO:119: WHRAGVRAKV
SEQ ID NO:120: FKRFWTGHR
SEQ ID NO:121: MMAWHARVAR
SEQ ID NO:122: WIWHRPIKVK
SEQ ID NO:123: WHRTLPKRGH
SEQ ID NO:124: VKHFRWRPVA
SEQ ID NO:125: KRHWRFQLSN
SEQ ID NO:126: KRHRLASMAP
SEQ ID NO:127: WRWRWRGVLR
SEQ ID NO:128: RLHAHHARHR
SEQ ID NO:129: RWGAKHRVRV
SEQ ID NO:130: AMGWRPVKHR
SEQ ID NO:131: KWRWRMHQHY
SEQ ID NO:132: WLSKLGHRHA
SEQ ID NO:133: KHCSIHTRLR
SEQ ID NO:134: GSAERMSEGH
SEQ ID NO:135: FPLWNVLTMT
SEQ ID NO:136: SFAGVGWFALLG
SEQ ID NO:137: CDLWVCFLDGGG
SEQ ID NO:138: LVARFPPPYGGV
SEQ ID NO:139: SIVWLTRKPG
SEQ ID NO:140: CRYRALNGVL
SEQ ID NO:141: ALTSRTWARQ
SEQ ID NO:142: TRYMLSRQSN
SEQ ID NO:143: AMREARITVK
SEQ ID NO:144: WRRHVPLRIL
SEQ ID NO:145: FHRWNRPMVT
SEQ ID NO:146: HRYKKTPVPM
SEQ ID NO:147: WLHVKRRPVV
SEQ ID NO:148: WVRHKHPIVP
SEQ ID NO:149: LSMRRRQFQS
SEQ ID NO:150: FHWRDKWRTG
SEQ ID NO:151: RMRRPGITVK
SEQ ID NO:152: GHRWNRPMVT
SEQ ID NO:153: WHRHTPKRIP
SEQ ID NO:154: WHWQRSRPAL
SEQ ID NO:155: KRTWWHYIRP and
SEQ ID NO:156: KRWRHSLPAS.

Further provided is a fragment of any of the above peptides wherein the fragment retains the ability to bind to monoclonal antibody SZ-2. The invention also provides an isolated molecule capable of binding to the above peptides (an anti-mimotope), and a method of modulating the adhesion, aggregation or agglutination of platelets by exposing the platelets to the anti-mimotope molecule.

The invention further provides a method of identifying a molecule that inhibits ristocetin induced aggregation of platelets. The method comprises determining whether a molecule binds to the isolated peptide of the subject invention (the mimotope peptide, such as the peptide comprising an amino acid sequence as shown in SEQ ID NO:174), and screening the molecule to determine whether the screened molecule inhibits ristocetin induced aggregation of platelets. If the molecule is a peptide, phage display libraries can be used to determine whether the molecule binds to the isolated peptide. If the molecule is an antibody, the antibody can be immobilized on a solid support and the peptide can be labeled with a detectable marker and contacted with the immobilized antibody. After washing, the presence of the label will indicate that the antibody (the anti-mimotope molecule) bound to the peptide. Likewise, the peptide could be immobilized and the antibody could be contacted with the immobilized peptide. These techniques are readily known in the art.

The invention is described in further detail as follows.

The C-34 Epitope

As reported by Miller, et al. (1990), platelets from patients with platelet-type von Willebrand disease (PT-vWD) heterozygous for the mutation 230.WKQ(G→V)$_{233}$V.234 in the alpha chain of platelet glycoprotein Ib were used as immunogens for the production of murine mabs. One such mab, C-34, inhibited ristocetin-induced aggregation of patient or normal platelets, but not aggregation induced by other aggregating agents. As demonstrated by crossed-immunoelectrophoresis, mab C-34 recognized an epitope within the GPIb/IX complex. In indirect immunofluorescence studies on fresh platelets, the ratio of any of four different anti-GPIb mabs to one another was near unity (0.88-1.14) both for normals and for patients. In contrast, the ratio of the binding of mab C-34 to such a mab (AP-1) was 0.31±0.02 (means±SE) for normal platelets and significantly increased to 0.54±0.01 for patient platelets (p<0.001). In immunoprecipitations on NP-40 lysates of $^3$H-labeled platelets, saturating concentrations of mab C-34 produced much fainter bands than did AS-2 or other anti-GPIb mabs. In contrast to the other anti-GPIb mabs, C-34 did not bind to the purified $^{125}$I-labeled glycocalicin fragment of GPIb or to the glycocalicin derivative identified by crossed-immunoelectrophoresis. In immunoprecipitation studies of $^3$H-labeled platelets subjected to digestion with trypsin or with chymotrypsin, C-34 identified neither the glycocalicin nor the amino-terminal 45 kDa fragment of GPIb alpha that were immunoprecipitated by mab AS-2 or by mab AS-7.

Thus, using three independent techniques (immunoprecipitation of platelet glycoproteins following radiolabeling of intact platelets and subsequent proteolytic digestion of these glycoproteins; immunoprecipitation of radiolabeled purified glycocalicin; crossed immunoelectrophoresis of platelet glycoproteins)(Miller et al. 1990), it has been shown that while C-34 recognizes an epitope within the GPIb/IX complex, this epitope does not appear to reside within glycocalicin.

While these studies reported a relatively simple method that succeeded in epitope mapping mabs AS-2 and AS-7 to the 45 kDa region of GPIb alpha, this work demonstrated that mab C-34 cannot be mapped to any single tryptic or chymotryptic domain of glycocalicin. Additionally, mab C-34 does not produce immunoprecipitation patterns similar to those of a mab recognizing GPIX.

Biopanning of Mab C-34 with Bacteriophage Display Libraries

Scott and Smith (1990) presented a method of defining peptide ligands by using randomly synthesized peptide inserts in bacteriophage. Related methods were published by Cwirla et al. (1990) and by Devlin et al. (1990). Since that time a literature has arisen in which both the original hexapeptide inserts and larger inserts have been used in identifying epitopes recognized by monoclonal antibodies. This technique has great potential for the detection of critical epitopes within the platelet vWF receptor known as GPIb/IX. The studies disclosed herein focus on monoclonal antibody C-34, but can be applied to other monoclonal antibodies having binding sites (epitopes) within GPIb/IX by the methods disclosed herein for mab C-34.

A well-balanced decapeptide (10-mer) library from Dr. Bruce Malcom of Alberta, Canada (described by Christian et al. 1992) and a dodecapeptide (12-mer) library from Clontech Laboratories (Palo Alto, Calif.) were used. In the dodecapeptide library, a reduced frequency of adenosines at the first two positions of each codon causes a characteristic underrepresentation of the following amino acids indicated by their one-letter codes: I,M,T,N,K,Y,H,Q,D, and E. The libraries have both been constructed into a Fuse 5 vector (Scott and Smith 1990) by the insertion of a mixture of synthetic oligonucleotides, with the random decapeptides (or modified-random dodecapeptides) fused to the minor viral coat protein pIII of the bacteriophage. The libraries each have a complexity of approximately $3 \times 10^8$ independent clones, and a titer of $10^{12}$ to $10^{14}$ per ml. While the Malcom library constitutes only a partial decapeptide library, it is complete as a hexapeptide library.

The strategy for using these libraries largely follows the review recently presented by Scott (1992) and employs, with modifications, the detailed methodology for use of this system as described recently by Smith and Scott (1993). The strategy used herein is as follows.

Specifically, in the first round of biopanning a 60 mm streptavidin-coated petri dish is filled with blocking solution (0.5% BSA, 0.1 M NaHCO$_3$, 0.1 µg/ml streptavidin, 0.2% NaN$_3$) for 2 hours, then washed three times with TBS-0.5% Tween. Next, 1 µl of the library (about $1 \times 10^{11}$ phage) that has been incubated overnight at 4° C. with 1 µg of biotinylated Mab is diluted with 1 ml of TBS-Tween, and this mixture is then added to the petri dish and rocked for 15 minutes at room temperature. The petri dish is washed 10 times with TBS-Tween, and bound phage is eluted by pipetting 800 µl of 0.1 N HCl (pH adjusted to 2.2 with glycine)-1 mg/ml BSA into the dish. The eluate is then pipetted into a microfuge tube containing 48 µl of 2M Tris, to bring the pH up to about 8.

The eluate is concentrated and washed twice in TBS using an Amicon Centricon-30 filter (Amicon, Inc., Beverly, Mass.). This final product is titered out by making dilutions from a small amount of concentrated eluate in TBS-0.1% gelatin and adding 1 µl of each dilution made to 19 µl of TBS-gelatin, then adding 20 µl of starved K91 E. coli cells and incubating for 10 minutes at room temperature. After adding 200 µl of NZY medium containing 0.2 µg/ml tetracycline (Tc) and incubating at 37° C. for 1 hour, the mixture is plated out on NZY agar plates containing 40 µg/ml tetracycline and allowed to grow up overnight at 37° C.

After titering, the entire concentrated eluate from the first round of biopanning (about 50 µl) is added to an equal volume of fresh starved K91 cells, and amplification performed as described by Smith and Scott (1993). Following the first PEG/NaCl precipitation, the resulting pellet is dissolved in 1 ml TBS. Phage is then precipitated a second time with PEG/NaCl, allowed to stand at least 1 hour at 4° C., and the precipitate collected following centrifugation at 4° C. After careful removal of all the supernatant, the pellet is dissolved in 100 µl TBS. This amplified product can then be titered.

The first round of biopanning results in a yield of $5 \times 10^{-7}$%. The second biopanning also used 1 µg of biotinylated C-34 with $1 \times 10^{11}$ phage, resulting in a yield of $4 \times 10^{-3}$%. The second round of biopanning is concentrated and amplified as in the first round. In the third round, 0.01 µg of biotinylated C-34 was biopanned against $2.5 \times 10^{11}$ phage, with a resulting yield of $3 \times 10^{-4}$%. The third round is stopped after eluting the bound phage from the petri dish. This eluate is not concentrated or amplified. Titerings are done before and after each round, and the percent yield is calculated as the number of bacteriophage obtained in an elution fraction relative to the initial number of bacteriophage (Christian et al. 1992). A yield should generally be greater than $10^{-5}$ to exceed background, with values of $10^{-4}$ to $10^{-1}$ typically observed. Increasing percent yields in subsequent rounds of biopanning are, in particular, suggestive that clones of increasing affinity are being selected.

For studies directed towards discovering a peptide binding the mimotope peptide (SEQ ID NO:1: AWNWRYREYV), two rounds of biopanning against the original decapeptide library were performed, using 1 µg of biotinylated mimotope peptide in the first round and 0.01 µg in the second round. Resulting yields were $3 \times 10^{-6}$% and $2 \times 10^{-3}$%, respectively.

In some experiments, an immunological screening assay, as described by Christian, et al. (1992) may be performed using NZY+Tc agar plates containing about 500 well-separated colonies. The colonies are transferred to nitrocellulose membrane filters (Biorad Laboratories, Hercules, Calif.), and the filters are immediately washed twice in TNT Buffer (10 mM Tris, pH 8.0, 150 mM NaCl, 0.05% Tween 20), blocked for 30 minutes at room temperature with gentle agitation in 20% normal goat serum in TNT buffer, then incubated for 2 hours at room temperature in primary mab that has been diluted 1:1000 in blocking buffer. The filters are washed sequentially for 10 minutes at room temperature each wash, in washing buffer A (TNT Buffer+0.1% BSA), washing buffer B (TNT Buffer+0.1% BSA+0.1% NP-40), and then again washing buffer A, and incubated in a secondary peroxidase-conjugated goat anti-mouse IgG for 1-½ hours at room temperature. The filters are washed as before, then put in a final wash of TN (10 mM Tris, pH. 7.5, 150 mM NaCl). Color development is observed after putting filters in ABTS substrate.

Small cultures of individual colonies are then grown up overnight, by either: a) selecting the colonies that were positive from the immunological screening; or b) skipping the screening step and randomly selecting colonies (about 100). Each colony is inoculated into 2 ml of NZY medium containing 20 µg/ml tetracycline, and these small cultures grown up overnight at 37° C., with vigorous shaking. The next day cultures are centrifuged to pellet the cells, and the supernatant is removed. To 1 ml of the supernatant is then added 150 µl PEG/NaCl, and the phage are precipitated overnight at 4° C. Following subsequent centrifugation and removal of supernatant, the pellet is dissolved in 1 ml TBS.

For DNA sequencing, 400 µl of the dissolved pellet is extracted once with phenol, and the resulting aqueous phase (about 300 µl) is added to 500 µl TE and 80 µl 3M sodium acetate buffer. Then 1 ml ethanol is added and the SS DNA is allowed to precipitate overnight at 4° C. Each sample is then microfuged for 30 minutes at 4° C., the DNA pellet washed once in 70% ETOH, dried, and resuspended in 7 µl $H_2O$. This template can be stored at –20° C. until ready to use.

Due to the quite GC-rich Sfi 1 cloning site flanking the insertion region (Christian et al. 1992), sequencing reactions are carried out using the Sequenase 7-deaza dGTP DNA sequencing kit (Amersham-US Biochemicals, Arlington Heights, Ill.) with $^{32}$P-dATP and an antisense primer located approximately 40 nucleotides 3' to the insert site (primer having SEQ ID NO:100: 5' CTCATAGTTAGCGTAACG-3'). Samples are run on a standard 6% sequencing gel using an IBI STS 45 sequencing apparatus (Eastman Kodak Company, Rochester, N.Y.).

The GCG software (Genetics Computer Group, Inc., Madison Wis.) is helpful for aligning sequences obtained from multiple clones in order to find consensus sequences. Certainly in the case of new mabs for which binding sites are sought, but even in the case of mab C-34, there is an interest in searching for sequences not only in GPIb alpha, but also in GPIb beta, GPIX, and in fact other platelet proteins that have been deposited in the available databases (Swiss Prot, Gen Bank, EMBL, etc.). Indeed, this analysis may provide important new information suggesting that a particular monoclonal antibody's epitope may be comprised of multiple components of the GPIb/IX complex that must accordingly be in close spatial proximity.

At this point, an ELISA assay can be used to evaluate individual clones, if the number of clones is high. In brief, phage having undergone two PEG precipitations, and subsequently adjusted for titer, can be incubated overnight with biotinylated mab, following which the mab-phage mixture can be added to wells of microtiter plates that have been previously coated with formalin-fixed platelets (or other suitable immobilized target recognized by the mab). Following a series of washing steps, avidin-peroxidase is added, the wells washed again, chromogenic substrate added, and the wells eventually read on an ELISA plate reader. The relative decrease in strength of signal in this assay provides guidance as to the most promising clones for further study. Consensus peptides identified in this manner can be chemically synthesized and characterized with respect to ability to bind original antibody. Peptides showing high binding affinity for the antibody can then be used as immunogens in mice and/or rabbits.

Epitope Mapping Studies of mab C-34

The two phage display libraries discussed above were employed in mapping studies with mab C-34. Results with the balanced, 10-mer peptide library were quite definitive with respect to strong consensus development among clones selected after two or three rounds of biopanning. Not only is there an evident consensus towards the 9-mer sequence SEQ ID NO: 38: W N W R Y R E Y V, but the 10-mer peptide including this sequence (SEQ ID NO: 1) with an amino-terminal alanine appeared to have the greatest selective advantage in the biopanning, since clones bearing this sequence were found the most frequently.

The series of cloned sequences is included in alignment form below. Double-underlines represent consensus amino acids and single-underlined amino acids represent significant homology to the consensus.

|  |  | Frequency |
|---|---|---|
| C34 Clone SEQ ID NO: 1: | .AWNWRYREYV | 52 |
| C34 Clone SEQ ID NO: 2: | .KWNWRNKKYV | 1 |
| C34 Clone SEQ ID NO: 3: | .LSTWRYFEYV | 14 |
| C34 Clone SEQ ID NO: 4: | .YLGWRYSEYV | 7 |
| C34 Clone SEQ ID NO: 5: | .TQMWRAREYL | 2 |
| C34 Clone SEQ ID NO: 6: | ....WRQREYWDPV | 1 |
| C34 Clone SEQ ID NO: 7: | .EGSWRYRKGG | 1 |
| C34 Clone SEQ ID NO: 8: | GYHWWRNWEY | 2 |
| C34 Clone SEQ ID NO: 9: | KGFLWRARNW | 1 |
| C34 Clone SEQ ID NO: 10: | MNWKHWRARH. | 1 |
| C34 Clone SEQ ID NO: 11: | FKWREWRGKL | 1 |
| C34 Clone SEQ ID NO: 12: | .PDRQVRLWVR | 1 |
| C34 Clone SEQ ID NO: 13: | RVLRHWHPRT | 1 |
| C34 Clone SEQ ID NO: 14: | .GRRVWMLNHG | 2 |
| C34 Clone SEQ ID NO: 15: | .KKGRHHVTRV | 22 |
| C34 Clone SEQ ID NO: 16: | .GGVCKCWQCL | 1 |
| C34 Clone SEQ ID NO: 17: | FSHSYGSAIR | 1 |
| C34 Clone SEQ ID NO: 18: | MHGHRRPGLA | 1 |
| C34 Clone SEQ ID NO: 19: | MSKKPHLGLR | 1 |
| C34 Clone SEQ ID NO: 20: | TMWVELYSLK | 1 |
| C34 Clone SEQ ID NO: 21: | FVDPGRAGRG | 1 |
| C34 Clone SEQ ID NO: 66: | KRAWWKQKWV | 1 |

Results with the second peptide display library that is partially restricted in its amino acid repertoire revealed a series of clones which bind to C-34 without any appearance of the mimotope consensus sequence SEQ ID NO:38. The series of cloned sequences from the second library is included in alignment form below. SEQ ID NO:22 is the native sequence of GPIb alpha from amino acid 484 to 499, and represents a possible natural epitope sequence revealed by the clones isolated from the second library. The ' represents potential chymotrypsin cleavage sites. As above, double-underlines represent the possible native sequence (SEQ ID NO:22) within this second library and single-underlined amino acids represent significant homology to the possible native sequence.

The following cloned sequences were also obtained from the second peptide display library:
SEQ ID NO:39: QVRLWARAGAGQ
SEQ ID NO:40: GLAVTFGSVLEG
SEQ ID NO:41: VRWMCVIRLGVR
SEQ ID NO:42: RLWGPGVSRPVL
SEQ ID NO:43: CGSSLFRGPRCP
SEQ ID NO:44: LGISSLSFLQLR
SEQ ID NO:45: TWGWDGVSYLFL
SEQ ID NO:46: TRSLFDDFVSLR
SEQ ID NO:47: CYASLFRSRLCA
SEQ ID NO:48: DGSVRVVWVRLL
SEQ ID NO:49: LSGFPVALVRFA
SEQ ID NO:50: LGGGLLVGSVFP
SEQ ID NO:51: VWARGVFRDRFF
SEQ ID NO:52: TGLLAGPVWRWT
SEQ ID NO:53: WLGGIFSCLVCG
SEQ ID NO:54: WFLRDVGCGSCL
SEQ ID NO:55: SRCGVFTWCSRS
SEQ ID NO:56: RCLVGYRCWGGV
SEQ ID NO:57: GFRCLVMGGGCA
SEQ ID NO:58: CGFDLVCARLFG
SEQ ID NO:59: DSGVRWFFGFLG
SEQ ID NO:60: ILDGCFFLGRCP
SEQ ID NO:61: CVRWLVSAGCSG
SEQ ID NO:62: CVGCWLVCDVLL
SEQ ID NO:63: CLFVFAAGFACG
SEQ ID NO:64: SCALFGSCFGIS
SEQ ID NO:65: CWGGVGVCGLLV
SEQ ID NO:67: CVGGVASRCGVL
SEQ ID NO:68: SGAVLAGPFGVW
SEQ ID NO:69: CRAFDRVGVCVW
SEQ ID NO:70: RCLVGYVVGGVW
SEQ ID NO:71: VCLVYRSVDCWA
SEQ ID NO:72: WRVFVFTCVVWA
SEQ ID NO:73: LWREWRGLFAVL
SEQ ID NO:74: SGAVLAGPLWRL
SEQ ID NO:75: FVVRGGTFLFVR
SEQ ID NO:77: TGLLAGPVWRWT
SEQ ID NO:78: DSGVRWFFGFLG
SEQ ID NO:79: CAWHRLSFCGLV
SEQ ID NO:80: CFGSALVLAVLA and
SEQ ID NO:81: WFWDMSGEWGGL.

Comparison of Consensus Sequence to Native Sequences

Considerable effort was extended in trying to relate the consensus sequence of the above peptide (SEQ ID NO:38) to native sequences within GPIb alpha or other known proteins in the Swiss Protein or NCBI data banks. No such relation was found. This sequence accordingly represents a "mimotope"—i.e., a peptide which mimics a native epitope (a binding site for a monoclonal antibody), despite a lack of apparent homology at the primary amino acid sequence level (for mimotopes, see: Motti et al. 1994, Larocca et al. 1992, Lenstra et al. 1992, Balass et al. 1993, Hobart et al. 1993, and Luzzago et al. 1993). As noted after reviewing SEQ ID NOs: 1-21 and 66 above, not all selected clones appear to be part of this consensus group, and it is possible that with further sequencing clues as to the native epitope may be derived.

By using the second peptide display library that is partially restricted in its amino acid repertoire, another series of clones ("C34b" series) binding to C-34 without appearance of the mimotope consensus peptides were obtained. Following sequencing of these clones, a FASTA analysis (Pearson and Lipman 1988; Pearson 1990) was performed upon this group of clones by moving a 7-amino acid window along the sequence of GPIb alpha, advancing one amino acid at a time, and determining the group score as a function of position in the GPIb alpha molecule.

The results do not, in general, offer compelling matches in the sense of consensus development among the clones. However, the possible native GPIb alpha sequence revealed by this analysis is represented by SEQ ID NO:22.

Aggregation Studies

Citrated human platelet-rich plasma (PRP) was prepared by standard methods (Miller et al. 1983). For study of C-34 neutralization by mimotope peptide, 350 µL of PRP containing 150,000 platelets/µL was incubated for 10 min at 22° C. with phosphate-buffered saline (PBS), 20 µg/mL C-34 mab, or 20 µg/mL C-34 that had previously been incubated for 30 min at 22° C. with varying concentrations of peptides. The PRP was then brought to 37° C. and stirred at 1200 rpm in a Chrono-Log lumi-aggregometer (Chrono-Log Corporation, Havertown, Pa.). Aggregation was initiated by the addition of 1 mg/mL ristocetin (Helena Laboratories, Beaumont, Tex.). For screening of bacteriophage clones displaying potential anti-mimotope peptides, 150 µl of PEG/NaCl precipitated phage was incubated with 250 µl of citrated PRP for one hour at 22° C., transferred to the aggregometer, following which ristocetin was added at a final concentration of 0.8 mg/ml. Study of the inhibitory potency of synthetic peptides upon vWF-dependent platelet aggregation was performed by preincubating 150 µL of varying dilutions of peptide dissolved in PBS, pH 6.0 for 2-4 hr at 22° C. with 250 µL of formalin-fixed (Macfarlane et al. 1975) platelets ($1.5 \times 10^5$/mL), following which the mixture was warmed to 37° C. in the aggregometer, purified vWF (Miller et al. 1983) (1 U/mL) was added, and aggregation was initiated by the addition of 0.9 mg/mL ristocetin.

Synthesized Peptide

A peptide including the consensus sequence (SEQ ID NO: 38) was chemically synthesized (Genosys Biotechnologies, The Woodlands, Texas). The synthesized peptide had an amino acid sequence corresponding to SEQ ID NO:1: AWNWRYREYV. A modification of this peptide with a biotin attached to the amino-terminal alanine (N-hydroxysuccinimide hexanoic acid long chain spacer arm biotinylation) was also synthesized. One mg of the chemically synthesized biotinylated peptide was dissolved in one ml of water containing 20 µl of DMSO. Since C-34 at a final concentration of 20 µg/mL is a potent inhibitor of ristocetin-induced aggregation in citrated platelet-rich plasma (PRP), the synthetic peptide's potency was assessed by examining whether the peptide could neutralize the inhibitory activity of C-34 in this setting. Accordingly, approximately 10 µg of C-34 was incubated at 22° C. for 30 minutes with varying concentrations of test or control peptide, following which the mixture was added to PRP in a final volume of approximately 0.5 ml for an additional 10 minutes at 22° C. As can be seen from the resulting aggregation curves (FIGS. 1-7), the synthesized peptide fully neutralized the C-34, producing half-maximal neutralization of the C-34 at about 1.0 µg/ml, which is approximately 0.55 µM for the biotinylated peptide. A similar pattern of C-34 antibody neutralization was observed when the non-biotinylated form of the peptide (having SEQ ID NO:38) was used, with half-maximal neutralization at approximately 3.0 µM. The peptide (native or biotinylated) by itself did not induce platelet aggregation, nor did it appear to have non-specific effects, inasmuch as it had no influence on ADP-induced aggregation.

More specifically, FIG. 1 shows the ristocetin-induced full aggregation of platelets in the presence of von Willebrand factor. FIG. 2 shows the inhibition of ristocetin-induced aggregation of platelets by 20 μg/ml of mab C-34. FIGS. 3-7 show varying degrees of neutralization of the inhibition of ristocetin-induced aggregation of platelets by 20 μg/ml of mab C-34 in the presence of 0.14, 0.27, 0.55, 1.1, and 2.3 μM of the synthetic biotinylated peptide mimotope having SEQ ID NO:1, respectively. In FIG. 3, 0.14 μM of the peptide does not neutralize the C-34 inhibition; in FIG. 7, 2.3 μM of the peptide fully neutralizes the C-34 inhibition, and FIGS. 4-6 show varying degrees of neutralization of the C-34 inhibition.

Additional Use of Synthesized Peptide

The chemically synthesized peptide can be conjugated to bovine serum albumin and used for raising polyclonal antibodies in rabbits. Standard procedures can be used to immunize the rabbits and to collect serum, as described below. Polyclonal antibody can be tested for its ability to bind to normal platelets, as well as to the wild-type and valine 233 mutant forms of recombinant GPIb alpha. For polyclonal antibody that shows a high affinity binding to platelets, functional studies can then be undertaken. These studies include adhesion, aggregation, agglutination, and vWF binding. F(ab)'$_2$ and Fab fragments of the polyclonal antibody can be made if steric hindrance appears to be preventing an accurate evaluation of more specific modulating effects of the antibody (Becker and Miller 1989, Kupinski and Miller 1986, and Miller et al. 1986). Polyclonal antibody to the synthetic peptide that recognizes or stabilizes a conformation associated with heightened or diminished affinity for binding vWF can be obtained at ≥95% purity and conjugated to bovine serum albumin or to another carrier protein, for the production of murine monoclonal antibodies.

Production of Antibodies to Synthesized Peptides

Mice: Monoclonal antibody production can be carried out using BALB/c mice. Immunization of the B-cell donor mice can involve immunizing them with antigens mixed in Titer-Max™ adjuvant as follows: 50 μg antigen/20 μl emulsion×2 injections given by an intramuscular injection in each hind flank on day 1. Blood samples can be drawn by tail bleeds on days 28 and 56 to check the titers by ELISA assay. At peak titer (usually day 56) the mice can be subjected to euthanasia by $CO_2$ inhalation, after which splenectomies can be performed and spleen cells harvested for the preparation of hybridomas by standard methods.

Rabbits: Polyclonal antibodies can be raised in New Zealand white rabbits. Preimmune serum can be collected from rabbits sedated with ketamine/rompun (ketamine HCl at 20 mg/kg IM and xylazine HCl at 4 mg/kg IM) via the auricular artery. Ten to fifteen percent of the total blood volume can be collected at each bleeding. The hair over the ear can be shaved with a #40 clipper blade, wiped with 70% alcohol, and a sterile 22 gauge butterfly can be used for blood collection. The antigen can be mixed with either RIBI adjuvant or TITER-MAX™ adjuvant and used according to the manufacturer's instructions. The back can then be shaved, wiped with 70% alcohol, and a sterile 25 gauge needle with the antigen/adjuvant mixture therein can be used to administer subcutaneously and intramuscularly as recommended by the manufacturer's instructions. Immune serum samples can be collected as described for preimmune samples. When sufficient titers are reached, the animal can be anesthetized with sodium pentobarbital (60 mg/kg BW) via the lateral ear vein until deep anesthesia is achieved. Blood can be immediately collected via cardiac puncture into plastic centrifuge tubes and allowed to clot; afterwards, the blood can be centrifuged and the serum aspirated and frozen at −70° C. For euthanasia, while under sodium pentobartital anesthesia at a dosage of 60 mg/kg, the rabbit can be exsanguinated via cardiac puncture.

Development of C-34 Anti-Mimotope Peptides

Figure 8:
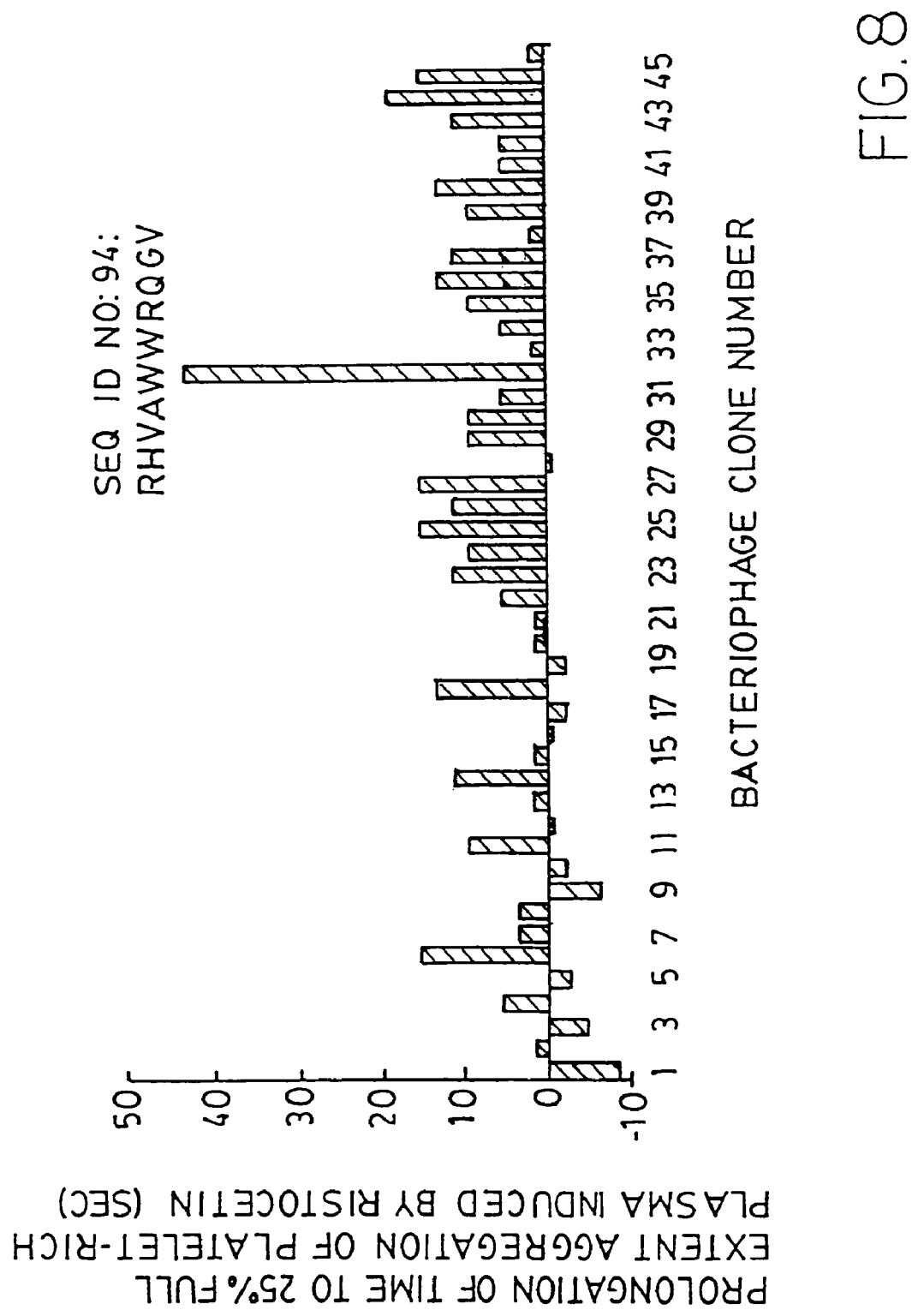

The mimotope decapeptide itself was then used as a probe to search for "anti-mimotope" peptides. Specifically, while a number of peptides might interact with some portion of the mimotope peptide exposed in solution, an "anti-mimotope" peptide would be defined as one that was not only selected in multiple rounds of biopanning, but that also provided some measure of functional interaction with the native epitope, thereby resembling the original monoclonal antibody. As shown in FIG. 8, one single clone of 46 bacteriophage clones purified and sequentially tested demonstrated inhibitory activity above background level in a functional platelet assay. This "anti-mimotope" clone displayed the sequence having SEQ ID NO:94: RHVAWWRQGV-the carboxyl terminal half of which is identical to residues 230-234 of GPIb alpha, with only the conservative (Lys→Arg) substitution at residue 231. (See GPIb alpha sequence from 225-237 [SEQ ID NO:101] and GPIb alpha sequence from 225-234 [SEQ ID NO:173: ENVYVWKQGV]). Of the 57 unique sequences ultimately determined, 5 additional sequences showed varying degrees of structural homology as shown below. Additional anti-mimotope sequences also included the following:

SEQ ID NO: 157: AYGVRHLGLS
SEQ ID NO: 158: KKWGQHRQRS
SEQ ID NO: 159: WRWMHWMPHA
SEQ ID NO: 160: WHWLARHRTV
SEQ ID NO: 161: RHRHRGFQPR
SEQ ID NO: 162: RGWRWHKYWQ
SEQ ID NO: 163: KRHAWMKSRL
SEQ ID NO: 164: LLLVGGSELT
SEQ ID NO: 165: KKVWMFSYNE
SEQ ID NO: 166: LSCRGCRAFV
SEQ ID NO: 167: HEGCEAQDEL
SEQ ID NO: 168: SVRHIWFHVK
SEQ ID NO: 169: GTWDLWRKGS
SEQ ID NO: 170: RWLWPRVHKT
SEQ ID NO: 171: HSPFRHVQPR and
SEQ ID NO: 172: WVRGHHREVR.

Figure 10:
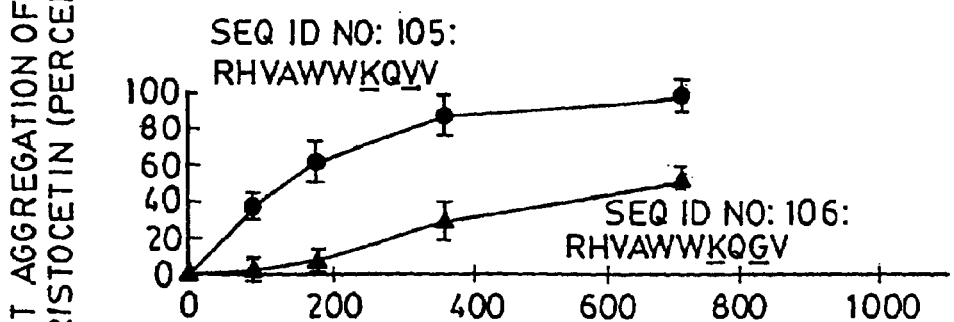
Figure 11:
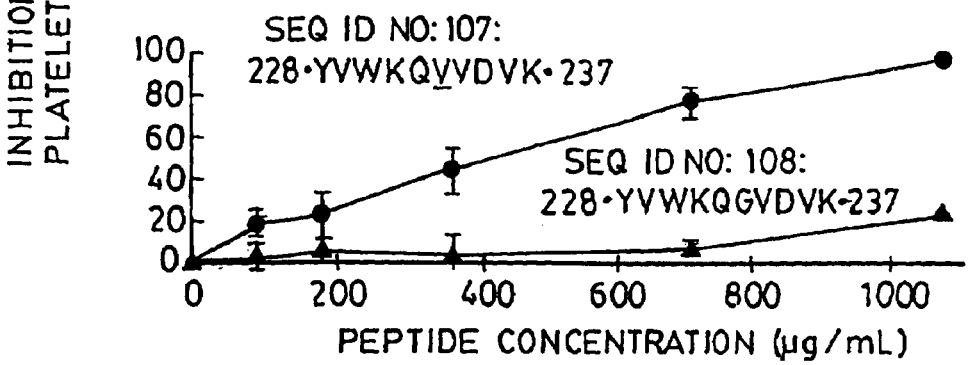

Further studies were undertaken with chemically synthesized peptide having SEQ ID NO:94: RHVAWWRQGV. This decapeptide was able to inhibit ristocetin-induced aggregation fully, with an $IC_{50}$ occurring between 200-400 μg/mL (FIG. 9). A (Gly→Val) substitution at position 9 (SEQ ID NO:104), corresponding to the mutation observed in PT-vWD, slightly lowered the $IC_{50}$, although nearly full inhibition was again seen by 715 μg/mL. In order to approximate more closely the native structure, peptides with an (Arg-Lys) substitution at position 7 were then studied. As shown in FIG. 10, a more dramatic difference between the Gly and the Val forms of the Lys-containing peptides was observed. Whereas the RHVAWW<u>K</u>QVV (SEQ ID NO:105) peptide retained potent inhibitory activity, the RHVAWW<u>K</u>QGV (SEQ ID NO:106) peptide was unable to exert more than slight inhibition, except at the highest concentrations tested. Finally, both the wild-type GPIb alpha 228-237 peptide (SEQ ID NO:108) containing Gly at residue 233 and the PT-vWD variant with Val replacing Gly at this position (SEQ ID NO:107) were synthesized. As shown in FIG. 11, the wild-type peptide was virtually without inhibitory activity. In contrast, the peptide corresponding to the PT-vWD mutant was capable of fully inhibiting ristocetin-induced aggregation, with an $IC_{50}$ of approximately 400 μg/mL. Lyophilized peptides were reconstituted in PBS, pH 6.0 and 150 μL of varying dilutions incubated for 2-4 hr at 22° C. with 250 μL of formalin-fixed platelets (1.5×10⁵/mL), prior to aggregometry in which the addition of 1 U/mL purified vWF was followed by the addition of 0.9 mg/mL ristocetin.

Three-Dimensional Description of Mimotope/Anti-Mimotope

FIGS. 12a-12c show the proposed three-dimensional description of mimotopes and anti-mimotopes. In FIG. 12a, the region within the extracellular domain of platelet glycoprotein Ib alpha containing the original epitope 10 capable of recognizing monoclonal antibody C-34 is shown. FIG. 12b shows the structure of the mimotope peptide 12 which mimics the original epitope (10, as shown in FIG. 12a) in three-dimensional space, without sharing the primary amino acid sequence of the original epitope. The mimotope peptide 12 also recognizes, or binds to, monoclonal antibody C-34.

FIG. 12c illustrates the structure of the mimotope peptide 12 in relation to the structure of the anti-mimotope peptide 14. The anti-mimotope peptide sequence is complementary to the face of the mimotope peptide in three-dimensional space, as monoclonal antibody C-34 was to the original epitope (see FIG. 12a).

Epitope Mapping Studies of mab SZ-2

Epitope mapping studies were also conducted using monoclonal antibody SZ-2. The choice of mab SZ-2 (Ruan et al. 1987) was made because its epitope is known to lie within the 45 kDa region of GPIb alpha (Fox et al. 1988; Molino et al. 1993); the epitope is likely to be relatively conformation-independent since SZ-2 blots strongly to GPIb alpha, glycocalicin or GPIb alpha 45 kDa fragment that has been denatured in SDS prior to transfer to nitrocellulose (Molino et al. 1993); and there may be widespread interest in epitope localization of this mab since it is available commercially and appears to be being used in a wide variety of investigative and clinical studies worldwide.

The well-balanced, 10-mer random peptide display library was used with SZ-2. Following either two or three rounds of biopanning with immunoscreening in the third round, bacteriophage clones were sequenced and the resulting predicted peptide sequences were analyzed for convergence upon a clear-cut pattern that hopefully is contained within the first ~300 amino acids of the mature GPIb alpha molecule. The resulting displayed sequences were compared with the available set of glycoprotein sequences known to exist on the platelet surface, including GPIa, GPIb alpha, GPIbβ, GPIIb, GPIIIa, GPIV, GPIX, and the platelet FCgamma₂ receptor.

The most convincing correspondence of multiple phage sequences with a natural platelet sequence may be with residues of the platelet FCgamma₂ receptor rather than of GPIb alpha, based upon the following observations: First, while GCG FASTA and WORDSEARCH analyses of phage sequences compared with residues 1-300 of GPIb alpha do show several favored regions of similarity, there is not yet a single, short stretch of amino acids in the native molecule that emerges in a convincing fashion as an obvious match. Second, using the first 50 clones for which highly purified PEG precipitates were prepared and titered, ELISA assays were performed in which the binding of phage to biotinylated SZ-2 inhibits the subsequent binding of the SZ-2 to immobilized glycocalicin. Only one of the 50 clones, displaying the sequence having SEQ ID NO:83: WHWRSSWKSG, proved capable of fully neutralizing SZ-2, and no other clone then available came even close in neutralizing potency. This clone, however, did not appear to represent an evident convergent pattern of the series of clones, nor did it provide a more extensive match to sequences within GPIb alpha than other clones then available. In computer-assisted analysis of the other platelet surface proteins, however, this sequence emerged as having the highest FASTA score for the region of the platelet FCgamma₂ receptor shown below, where it is shown as the second peptide in a proposed consensus sequence list. Several additional clones were sequenced, which yielded the peptide shown first in the series —SEQ ID NO:84: HRPLSWKGRA. Note that this peptide also has the SWK sequence, but additionally has an R three residues amino to the SWK. Below the convergence sequence mapped to the platelet FCgamma₂ receptor is shown in the sequence within GPIb alpha that would most closely match the proposed consensus set.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Balass, M. et al., Proc Natl Acad Sci USA 90: 10638-10642 (November 1993).
Becker, B. H. and Miller, J. L., Blood 74: 690-694 (1989).
Chambers, M. et al., in *Leucocyte Typing V: White Cell Differentiation Antigens*, ed. Schlossman, S., pp. 1343-1345, Oxford University Press, New York (1995).
Christian, R. B. et al., J Mol Biol 227: 711-718 (1992).
Clemetson, K. J. and Clemetson, J. M., Sem. Thromb. Hemost. 21: 130-136 (1995).
Clemetson, K. J. and Hugli, B., in *Leucocyte Typing V: White Cell Differentiation Antigens*, ed. Schlossman, S., pp. 1323-1325 Oxford University Press, New York (1995).
Cwirla, S. E. et al., Proc Natl Acad Sci USA 87: 6378-6382 (August 1990).
Devlin, J. J. et al., Science 249: 404-406 (1990).
Du, X. et al., Blood 69: 1524-1527 (1987).
Fitzgerald, L. A. and Phillips, D. R., in *Platelet Immunobiology: Molecular and Clinical Aspects*, Kunicki, T. J. and George, J. N., Eds., pp. 9-30, Lippincott, Philadelphia Pa. (1989).
Fox, J. E. B. et al., J. Biol Chem 263: 4882-4890 (1988).
Hobart, M. J. et al., Proc R Soc London B 252: 157-162 (1993).
Joyce, G. F., Current Opinion in Structural Biology 4: 331-336 (1994).
Kupinski, J. M. and Miller, J. L., Thromb Res 43: 335-344 (1986).
LaRocca, D. et al., Hybridoma 11: 191-201 (1992).
Lenstra, J. A. et al., J Immunol Methods 152: 149-157 (1992).
Lopez, J. A., Blood Coag. & Fibrinolysis 5: 97-119 (1994).
Luzzago, A. et al., Gene 128: 51-57 (1993).
Macfarlane, D. E., et al. Thrombos Diath Haemorrh 34: 306-308 (1975).
Miller, J. L. and Castella, A., Blood 60: 790-794 (1982).
Miller, J. L. et al., J Clin Invest 72: 1532-1542 (1983).
Miller, J. L. et al., Blood 68: 743-751 (1986).
Miller, J. L. et al., Blood 70: 1804-1809 (1987).
Miller, J. L. et al., Br J Haemotol 74: 313-319 (1990).
Miller, J. L. et al., Proc Natl Acad Sci USA 88: 4761-4765 (1991).
Miller, J. L. et al., Blood 79: 439-446 (1992).
Molino, M. et al., Blood 82: 2442-2451 (1993).
Motti, C. et al., Gene 146: 191-198 (1994).
Murata, M., et al., J Clin Invest 92: 1555-1558 (1993).

Parmley, S. F. and Smith, G. P., Gene 73: 305-318 (1988).
Pearson, W. R. and Lipman, D. J., Proc Natl Acad Sci USA 85: 2444-2448 (1988).
Pearson, W. R., Methods in Enzymology 183: 63-98 (1990).
Roth, G. J., Blood 77: 5-19 (1991).
Ruan, C. et al., Blood 69: 570-577 (1987).
Russell, S. D. and Roth, G. J., Blood 81: 1787-1791 (1993).
Scott, J. K., Trends in Biochem Sci 17: 241-245 (1992).
Scott, J. K. and Smith, G. P., Science 249: 386-390 (Jul. 27, 1990).

Smith, G. P. and Scott, J. K., Methods in Enzymology 217: 228-257 (1993).

Takahashi, H. et al., Thromb Res 19: 857-867 (1980).
Takahashi, H. et al., Blood 85: 727-733 (1995).
Ward, C. M. and Berndt, M. C., in *Leucocyte Typing V: White Cell Differentiation Antigens*, ed. Schlossman, S., pp. 1336-1337, Oxford University Press, New York (1995).
Weiss, H. J. et al., N Engl J Med 306: 326-362 (1982).

What is claimed is:

1. An isolated peptide comprising the amino acid sequence as shown in SEQ ID NO:174, provided that said isolated peptide does not have the amino acid sequence as shown in SEQ ID NO:1, SEQ ID NO:3, SEQ ID NO:4, SEQ ID NO:5, SEQ ID NO:6, SEQ ID NO:8, or SEQ ID NO:38, and further provided that said isolated peptide is capable of binding to at least one peptide consisting of the amino acid sequence selected from the group consisting of:

SEQ ID NO:94: RHVAWWRQGV
SEQ ID NO:95: AKHRWWRRPV
SEQ ID NO:96: KHFMRHRHGV
SEQ ID NO:97: AGLNHWWKHK
SEQ ID NO:98: RRSTWHWWHA
SEQ ID NO:99: VAKWRHWNRQ
SEQ ID NO:157: AYGVRHLGLS
SEQ ID NO:158: KKWGQHRQRS
SEQ ID NO:159: WRWMHWMPHA
SEQ ID NO:160: WHWLARHRTV
SEQ ID NO:161: RHRHRGFQPR
SEQ ID NO:162: RGWRWHKYWQ
SEQ ID NO:163: KRHAWMKSRL
SEQ ID NO:164: LLLVGGSELT
SEQ ID NO:165: KKVWMFSYNE
SEQ ID NO:166: LSCRGCRAFV
SEQ ID NO:167: HEGCEAQDEL
SEQ ID NO:168: SVRHIWFHVK
SEQ ID NO:169: GTWDLWRKGS
SEQ ID NO:170: RWLWPRVHKT
SEQ ID NO:171: HSPFRHVQPR and
SEQ ID NO:172: WVRGHHREVR.

2. The isolated peptide of claim 1 wherein amino acid residue number 3 of SEQ ID NO:174 is selected from the group consisting of alanine, asparagine, glutamine, and tyrosine.

3. The isolated peptide of claim 1 wherein amino acid residue number 4 of SEQ ID NO:174 is selected from the group consisting of arginine, phenylalanine, serine, and tryptophan.

4. The isolated peptide of claim 1 wherein amino acid residue number 3 of SEQ ID NO:174 is selected from the group consisting of alanine, asparagine, glutamine, and tyrosine; and wherein amino acid residue number 4 of SEQ ID NO:174 is selected from the group consisting of arginine, phenylalanine, serine, and tryptophan.

5. The isolated peptide of claim 1 wherein amino acid residue number 3 of SEQ ID NO:174 is tyrosine.

6. The isolated peptide of claim 1 wherein amino acid residue number 3 of SEQ ID NO:174 is tyrosine; and wherein amino acid residue number 4 of SEQ ID NO:174 is selected from the group consisting of arginine, phenylalanine, serine, and tryptophan.

7. The isolated peptide of claim 1 wherein amino acid residue number 3 of SEQ ID NO:174 is tyrosine; and wherein amino acid residue number 4 of SEQ ID NO:174 is selected from the group consisting of arginine, phenylalanine, and serine.

8. The isolated peptide of claim 1 wherein amino acid residue number 4 of SEQ ID NO:174 is arginine.

9. The isolated peptide of claim 1 wherein amino acid residue number 4 of SEQ ID NO:174 is arginine; and wherein amino acid residue number 3 of SEQ ID NO:174 is selected from the group consisting of alanine, asparagine, glutamine, and tyrosine.

10. The isolated peptide of claim 1 wherein amino acid residue number 4 of SEQ ID NO:174 is arginine; and wherein amino acid residue number 3 of SEQ ID NO:174 is selected from the group consisting of alanine, glutamine, and tyrosine.

11. The isolated peptide of claim 1 wherein amino acid residue number 3 of SEQ ID NO:174 is asparagine; and wherein amino acid residue number 4 of SEQ ID NO:174 is tryptophan.

* * * * *